(12) United States Patent
Walters et al.

(10) Patent No.: US 8,591,393 B2
(45) Date of Patent: Nov. 26, 2013

(54) CATHETER PUMP

(75) Inventors: Daniel A. Walters, Rockaway Township, NJ (US); William James Repka, Parsippany-Troy Hills, NJ (US); Brian A. Prais, Salisbury Mills, NY (US); Jonathan R. Williams, Montville, NJ (US)

(73) Assignee: Thoratec Corporation, Pleasanton, CA (US)

( * ) Notice: Subject to any disclaimer, the term of this patent is extended or adjusted under 35 U.S.C. 154(b) by 42 days.

(21) Appl. No.: 13/344,544

(22) Filed: Jan. 5, 2012

(65) Prior Publication Data

US 2012/0178985 A1     Jul. 12, 2012

Related U.S. Application Data

(60) Provisional application No. 61/430,171, filed on Jan. 6, 2011, provisional application No. 61/430,517, filed on Jan. 6, 2011.

(51) Int. Cl.
*A61N 1/362*     (2006.01)

(52) U.S. Cl.
USPC ............................................................ 600/16

(58) Field of Classification Search
USPC ............................................................ 600/16
See application file for complete search history.

(56) References Cited

U.S. PATENT DOCUMENTS

| | | |
|---|---|---|
| 1,902,418 A | 3/1933 | Pilgrim |
| 2,356,659 A | 10/1942 | Aguiar |
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |

(Continued)

FOREIGN PATENT DOCUMENTS

| | | |
|---|---|---|
| CA | 2367469 | 10/2000 |
| EP | 0 533 432 | 9/1992 |

(Continued)

OTHER PUBLICATIONS

Extended European Search Report dated Oct. 8, 2012, received in European Patent Application No. 07753903.9.

(Continued)

*Primary Examiner* — George Manuel
(74) *Attorney, Agent, or Firm* — Knobbe Martens Olson & Bear LLP

(57) ABSTRACT

A heart pump is provided that comprises an elongate catheter body, an impeller disposed at the distal end of the elongate catheter body, and one or more bearings positioned between the catheter body and the impeller. A fluid supply line for delivering infusant into the catheter is provided. A fluid return line for transporting infusant out of the catheter is also provided. A pump assembly for regulating the infusant flow along the fluid supply line and fluid return line is provided as part of an infusion system.

23 Claims, 21 Drawing Sheets

(56) References Cited

U.S. PATENT DOCUMENTS

| | | | |
|---|---|---|---|
| 3,904,901 A | 9/1975 | Renard et al. | |
| 3,995,617 A | 12/1976 | Watkins et al. | |
| 4,129,129 A | 12/1978 | Amrine | |
| 4,135,253 A | 1/1979 | Reich et al. | |
| 4,149,535 A | 4/1979 | Volder | |
| 4,304,524 A | 12/1981 | Coxon et al. | |
| 4,382,199 A * | 5/1983 | Isaacson | 310/87 |
| 4,392,836 A | 7/1983 | Sugawara | |
| 4,458,366 A | 7/1984 | MacGregor | |
| 4,540,402 A | 9/1985 | Aigner | |
| 4,589,822 A | 5/1986 | Clausen et al. | |
| 4,625,712 A | 12/1986 | Wampler | |
| 4,655,745 A | 4/1987 | Corbett | |
| 4,686,982 A | 8/1987 | Nash | |
| 4,704,121 A | 11/1987 | Moise | |
| 4,753,221 A | 6/1988 | Kensey et al. | |
| 4,769,006 A | 9/1988 | Papantonakos | |
| 4,817,586 A | 4/1989 | Wampler | |
| 4,846,152 A | 7/1989 | Wampler et al. | |
| 4,895,557 A | 1/1990 | Moise et al. | |
| 4,900,227 A | 2/1990 | Trouplin | |
| 4,902,272 A | 2/1990 | Milder et al. | |
| 4,906,229 A | 3/1990 | Wampler | |
| 4,908,012 A | 3/1990 | Moise et al. | |
| 4,919,647 A | 4/1990 | Nash | |
| 4,944,722 A | 7/1990 | Carriker et al. | |
| 4,955,856 A | 9/1990 | Phillips | |
| 4,957,504 A | 9/1990 | Chardack | |
| 4,964,864 A | 10/1990 | Summers et al. | |
| 4,969,865 A | 11/1990 | Hwang et al. | |
| 4,976,270 A | 12/1990 | Parl et al. | |
| 4,985,014 A | 1/1991 | Orejola | |
| 4,994,017 A | 2/1991 | Yozu | |
| 4,995,857 A | 2/1991 | Arnold | |
| 5,021,048 A | 6/1991 | Buckholtz | |
| 5,049,134 A | 9/1991 | Golding et al. | |
| 5,089,016 A | 2/1992 | Millner et al. | |
| 5,092,844 A | 3/1992 | Schwartz et al. | |
| 5,098,256 A | 3/1992 | Smith | |
| 5,106,368 A | 4/1992 | Uldall et al. | |
| 5,112,200 A | 5/1992 | Isaacson et al. | |
| 5,112,349 A | 5/1992 | Summers et al. | |
| 5,129,883 A | 7/1992 | Black | |
| 5,147,186 A | 9/1992 | Buckholtz | |
| 5,163,910 A | 11/1992 | Schwartz et al. | |
| 5,171,212 A | 12/1992 | Buck et al. | |
| 5,190,528 A | 3/1993 | Fonger et al. | |
| 5,201,679 A | 4/1993 | Velte et al. | |
| 5,211,546 A | 5/1993 | Isaacson et al. | |
| 5,290,227 A | 3/1994 | Pasque | |
| 5,300,112 A | 4/1994 | Barr | |
| 5,312,341 A | 5/1994 | Turi | |
| 5,346,458 A | 9/1994 | Affeld | |
| 5,360,317 A | 11/1994 | Clausen et al. | |
| 5,376,114 A | 12/1994 | Jarvik | |
| 5,405,383 A | 4/1995 | Barr | |
| 5,437,541 A | 8/1995 | Vainrub et al. | |
| 5,449,342 A | 9/1995 | Hirose et al. | |
| 5,458,459 A | 10/1995 | Hubbard et al. | |
| 5,505,701 A | 4/1996 | Anaya Fernandez de Lomana | |
| 5,527,159 A | 6/1996 | Bozeman, Jr. et al. | |
| 5,533,957 A | 7/1996 | Aldea | |
| 5,588,812 A | 12/1996 | Taylor et al. | |
| 5,613,935 A | 3/1997 | Jarvik | |
| 5,643,226 A | 7/1997 | Cosgrove et al. | |
| 5,678,306 A | 10/1997 | Bozeman, Jr. et al. | |
| 5,692,882 A | 12/1997 | Bozeman, Jr. et al. | |
| 5,707,218 A | 1/1998 | Maher et al. | |
| 5,722,930 A | 3/1998 | Larson et al. | |
| 5,738,649 A | 4/1998 | Macoviak | |
| 5,741,234 A | 4/1998 | Aboul-Hosn | |
| 5,746,709 A | 5/1998 | Rom et al. | |
| 5,749,855 A | 5/1998 | Reitan | |
| 5,755,784 A | 5/1998 | Jarvik | |
| 5,776,111 A | 7/1998 | Tesio | |
| 5,807,311 A | 9/1998 | Palestrant | |
| 5,814,011 A | 9/1998 | Corace | |
| 5,824,070 A | 10/1998 | Jarvik | |
| 5,851,174 A | 12/1998 | Jarvik et al. | |
| 5,868,702 A | 2/1999 | Stevens | |
| 5,868,703 A | 2/1999 | Bertolero | |
| 5,888,242 A | 3/1999 | Antaki et al. | |
| 5,911,685 A | 6/1999 | Siess et al. | |
| 5,921,913 A | 7/1999 | Siess | |
| 5,941,813 A | 8/1999 | Sievers et al. | |
| 5,951,263 A | 9/1999 | Taylor et al. | |
| 5,964,694 A | 10/1999 | Siess et al. | |
| 6,007,478 A | 12/1999 | Siess et al. | |
| 6,007,479 A | 12/1999 | Rottenberg et al. | |
| 6,015,272 A | 1/2000 | Antaki et al. | |
| 6,056,719 A | 5/2000 | Mickley | |
| 6,058,593 A | 5/2000 | Siess | |
| 6,071,093 A | 6/2000 | Hart | |
| 6,083,260 A | 7/2000 | Aboul-Hosn | |
| 6,086,527 A | 7/2000 | Talpade | |
| 6,086,570 A | 7/2000 | Aboul-Hosn et al. | |
| 6,113,536 A | 9/2000 | Aboul-Hosn et al. | |
| 6,123,659 A | 9/2000 | Le Blanc et al. | |
| 6,123,725 A | 9/2000 | Aboul-Hosn | |
| 6,132,363 A | 10/2000 | Freed et al. | |
| 6,135,943 A | 10/2000 | Yu et al. | |
| 6,136,025 A | 10/2000 | Barbut et al. | |
| 6,139,487 A | 10/2000 | Siess | |
| 6,152,704 A | 11/2000 | Aboul-Hosn et al. | |
| 6,176,822 B1 | 1/2001 | Nix et al. | |
| 6,176,848 B1 | 1/2001 | Rau et al. | |
| 6,190,304 B1 | 2/2001 | Downey et al. | |
| 6,200,260 B1 | 3/2001 | Bolling | |
| 6,210,133 B1 | 4/2001 | Aboul-Hosn et al. | |
| 6,210,397 B1 | 4/2001 | Aboul-Hosn et al. | |
| 6,227,797 B1 | 5/2001 | Watterson et al. | |
| 6,228,063 B1 | 5/2001 | Aboul-Hosn | |
| 6,234,960 B1 | 5/2001 | Aboul-Hosn et al. | |
| 6,245,007 B1 | 6/2001 | Bedingham et al. | |
| 6,247,892 B1 | 6/2001 | Kazatchkov et al. | |
| 6,248,091 B1 | 6/2001 | Voelker | |
| 6,254,359 B1 | 7/2001 | Aber | |
| 6,287,319 B1 | 9/2001 | Aboul-Hosn et al. | |
| 6,295,877 B1 | 10/2001 | Aboul-Hosn et al. | |
| 6,387,037 B1 | 5/2002 | Bolling et al. | |
| 6,395,026 B1 | 5/2002 | Aboul-Hosn et al. | |
| 6,422,990 B1 | 7/2002 | Prem | |
| 6,425,007 B1 | 7/2002 | Messinger | |
| 6,428,464 B1 | 8/2002 | Bolling | |
| 6,447,441 B1 | 9/2002 | Yu et al. | |
| 6,508,777 B1 | 1/2003 | Macoviak et al. | |
| 6,508,787 B2 | 1/2003 | Erbel et al. | |
| 6,517,315 B2 | 2/2003 | Belady | |
| 6,532,964 B2 | 3/2003 | Aboul-Hosn et al. | |
| 6,533,716 B1 | 3/2003 | Schmitz-Rode et al. | |
| 6,544,216 B1 | 4/2003 | Sammler et al. | |
| 6,547,519 B2 | 4/2003 | de Blanc et al. | |
| 6,609,883 B2 | 8/2003 | Woodard et al. | |
| 6,610,004 B2 | 8/2003 | Viole et al. | |
| 6,613,008 B2 | 9/2003 | Aboul-Hosn et al. | |
| 6,616,323 B2 | 9/2003 | McGill | |
| 6,623,420 B2 | 9/2003 | Reich et al. | |
| 6,641,558 B1 | 11/2003 | Aboul-Hosn et al. | |
| 6,692,318 B2 | 2/2004 | McBride | |
| 6,709,418 B1 | 3/2004 | Aboul-Hosn et al. | |
| 6,716,189 B1 | 4/2004 | Jarvik et al. | |
| 6,749,598 B1 | 6/2004 | Keren et al. | |
| 6,776,578 B2 | 8/2004 | Belady | |
| 6,783,328 B2 | 8/2004 | Lucke et al. | |
| 6,790,171 B1 | 9/2004 | Grundeman et al. | |
| 6,794,789 B2 | 9/2004 | Siess et al. | |
| 6,814,713 B2 | 11/2004 | Aboul-Hosn et al. | |
| 6,817,836 B2 | 11/2004 | Nose et al. | |
| 6,860,713 B2 | 3/2005 | Hoover | |
| 6,866,625 B1 | 3/2005 | Avre et al. | |
| 6,889,082 B2 | 5/2005 | Bolling et al. | |
| 6,926,662 B1 | 8/2005 | Aboul-Hosn et al. | |
| 6,935,344 B1 | 8/2005 | Aboul-Hosn et al. | |
| 6,942,611 B2 | 9/2005 | Siess | |

(56) References Cited

U.S. PATENT DOCUMENTS

| | | |
|---|---|---|
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,284,956 B2 | 10/2007 | Nose et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride |
| 7,491,163 B2 | 2/2009 | Viole et al. |
| 7,605,298 B2 | 10/2009 | Bechert et al. |
| 7,619,560 B2 | 11/2009 | Penna |
| 7,731,675 B2 | 6/2010 | Aboul-Hosn et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,819,833 B2 | 10/2010 | Ainsworth et al. |
| 7,828,710 B2 | 11/2010 | Shifflette |
| 7,841,976 B2 | 11/2010 | Mc Bride et al. |
| 7,927,068 B2 | 4/2011 | McBride et al. |
| 7,942,804 B2 | 5/2011 | Khaw |
| 7,942,844 B2 | 5/2011 | Moberg et al. |
| 7,993,259 B2 | 8/2011 | Kang et al. |
| 7,998,054 B2 | 8/2011 | Bolling |
| 8,079,948 B2 | 12/2011 | Shifflette |
| 8,110,267 B2 | 2/2012 | Houston et al. |
| 8,177,703 B2 | 5/2012 | Smith et al. |
| 8,206,350 B2 | 6/2012 | Mann et al. |
| 2002/0151761 A1 | 10/2002 | Beizai et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0165269 A9 | 7/2005 | Aboul-Hosn et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2008/0103442 A1 | 5/2008 | Kesten et al. |
| 2008/0103591 A1 | 5/2008 | Siess |
| 2008/0167679 A1 | 7/2008 | Papp |
| 2008/0275290 A1 | 11/2008 | Viole et al. |
| 2009/0023975 A1 | 1/2009 | Marseille et al. |
| 2009/0062597 A1 | 3/2009 | Shifflette |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0171137 A1 | 7/2009 | Farnan et al. |
| 2009/0182188 A1 | 7/2009 | Marseille et al. |
| 2010/0087773 A1 | 4/2010 | Ferrari |
| 2010/0127871 A1 | 5/2010 | Pontin |
| 2010/0197994 A1 | 8/2010 | Mehmanesh |
| 2010/0210895 A1 | 8/2010 | Aboul-Hosn et al. |
| 2010/0286210 A1 | 11/2010 | Murata et al. |
| 2011/0004046 A1 | 1/2011 | Campbell et al. |
| 2011/0021865 A1 | 1/2011 | Aboul-Hosn et al. |
| 2011/0034874 A1 | 2/2011 | Reitan |
| 2011/0071338 A1 | 3/2011 | McBride et al. |
| 2011/0076439 A1 | 3/2011 | Zeilon |
| 2011/0236210 A1 | 9/2011 | McBride et al. |
| 2011/0257462 A1 | 10/2011 | Rodefeld |
| 2012/0004495 A1 | 1/2012 | Bolling |
| 2012/0172655 A1 | 7/2012 | Campbell et al. |
| 2012/0172656 A1 | 7/2012 | Walters et al. |
| 2012/0178986 A1 | 7/2012 | Campbell et al. |

FOREIGN PATENT DOCUMENTS

| | | |
|---|---|---|
| EP | 1207934 | 5/2002 |
| EP | 2151257 A1 | 2/2010 |
| EP | 2 263 732 A2 | 12/2010 |
| FR | 2267800 | 4/1974 |
| JP | S48-23295 | 3/1973 |
| JP | H06-114101 | 4/1994 |
| JP | H08-196624 | 8/1996 |
| JP | 10-099447 | 4/1998 |
| JP | 2002-505168 | 2/2002 |
| JP | 2011-000620 | 9/2005 |
| JP | 2011-157961 | 8/2011 |
| WO | WO 89/04644 | 6/1989 |
| WO | WO 89/05164 A1 | 6/1989 |
| WO | WO 97/15228 | 5/1997 |
| WO | WO 99/37352 | 7/1999 |
| WO | WO 00/12148 | 3/2000 |
| WO | WO 00/18448 | 4/2000 |
| WO | WO 00/19097 | 4/2000 |
| WO | WO 00/43053 | 7/2000 |
| WO | WO 00/61207 | 10/2000 |
| WO | WO 00/69489 | 11/2000 |
| WO | WO 01/24867 | 4/2001 |
| WO | WO 02/070039 | 9/2002 |
| WO | WO 03/068303 | 8/2003 |
| WO | WO 03/103745 | 12/2003 |
| WO | WO 2005/089674 | 9/2005 |
| WO | WO 2005/123158 | 12/2005 |
| WO | WO 2007/112033 | 10/2007 |
| WO | WO 2008-034068 | 3/2008 |
| WO | WO 2009/073037 | 6/2009 |
| WO | WO 2010/127871 | 11/2010 |
| WO | WO 2010/149393 | 12/2010 |
| WO | WO 2011/003043 | 1/2011 |
| WO | WO 2011/035926 | 3/2011 |
| WO | WO 2011/035929 | 3/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |

OTHER PUBLICATIONS

ABIOMED—Recovering hearts. Saving lives., Impella 2.5 System, Instructions for Use, Jul. 2007, 86 sheets.

Cardiovascular Diseases (CVDs) Fact Sheet No. 317. World Health Organization. [Online] Sep. 2011. http://www.who.int/mediacentre/factsheets/fs317/en/index.html, accessed on Aug. 29, 2012.

European Search Report received from the European Patent Office in EP Application No. EP 05799883.3 dated May 10, 2011, 4 pages.

Ide, Hirofumi et al., Evaluation of the Pulsatility of a New Pulsatile Left Ventricular Assist Device—the Integrated Cardioassist Catheter—in Dogs, J. of Thoracic and Cardiovascular Surgery 107 (2): 569-75; Feb. 1994.

Ide, Hirofumi et al., Hemodynamic Evaluation of a New Left Ventricular Assist Device, Artificial Organs 16 (3): 286-90; 1992.

International Preliminary Examination Report from the European Patent Office received in PCT Application No. PCT/US2003/04853, mailed Jul. 26, 2004, 5 pages.

International Preliminary Examination Report from the European Patent Office received in PCT Application No. PCT/US2003/04401, mailed May 18, 2004, 4 pages.

(56) References Cited

OTHER PUBLICATIONS

International Preliminary Report on Patentability and Written Opinion of the International Searching Authority received in PCT Application No. PCT/US2005/033416, mailed Mar. 20, 2007, 7 pages.
International Preliminary Report on Patentability of the International Searching Authority received in PCT Application No. PCT/US2007/007313, mailed Sep. 23, 2008, 6 pages.
International Search Report and Written Opinion received in PCT Application No. PCT/US2005/33416, mailed Dec. 11, 2006, 4 pages.
International Search Report and Written Opinion received in PCT Application No. PCT/US2007/07313, mailed Mar. 4, 2008, 8 pages.
International Search Report received in PCT Application No. PCT/US2003/04401, mailed Nov. 10, 2003, 9 pages.
International Search Report received in PCT Application No. PCT/US2003/04853, mailed Jul. 3, 2003, 3 pages.
International Search Report Written Opinion received in PCT Application No. PCT/US2010/040847 mailed on Dec. 14, 2010.
International Search Report and Written Opinion received in PCT Application No. PCT/US2012/020382, mailed Jul. 31, 2012.
International Search Report and Written Opinion received in PCT Application No. PCT/US2012/020369 mailed Jul. 30, 2012.
International Search Report and Written Opinion received in PCT Application No. PCT/US2012/020553 mailed Aug. 17, 2012.
International Search Report and Written Opinion received in PCT Application No. PCT/US2012/020383 mailed Aug. 17, 2012.
Mihaylov, D. et al., Evaluation of the Optimal Driving Mode During Left Ventricular Assist with Pulsatile Catheter Pump in Calves, Artificial Organs 23(12): 1117-22; 1999.
Mihaylov, Dimiter et al., Development of a New Introduction Technique for the Pulsatile Catheter Pump, Artificial Organs 21(5): 425-27; 1997.
Morsink, PLJ et al., Numerical Modelling of Blood Flow Behaviour in the Valved Catheter of the PUCA Pump, a LVAD, The International Journal of Artificial Organs 20(5): 277-284; 1997.
Nishimura et al. The enabler cannula pump: a novel circulatory support system. The International Journal of Artificial Organs, vol. 22, No. 5, 1999, pp. 317-323.
Rakhorst, Gerhard et al., In Vitro Evaluation of the Influence of Pulsatile Intraventricular Pumping on Ventricular Pressure Patterns, Artificial Organs 18(7): 494-99; 1994.
Reitan, Oyvind, et al., Hydrodynamic Properties of a New Percutaneous Intra-aortic Axial Flow Pump. Reitan et al. ASAIO Journal 2000. pp. 323-328.
Schmitz-Rode, Thomas et al., "An Expandable Percutaneous Catheter Pump for Left Ventricular Support", Journal of the American College of Cardiology, vol. 45, No. 11, 2005, pp. 1856-1861.
Sharony et al. Cardiopulmonary Support and Physiology—The Intra-Aortic Cannula Pump: A Novel Assist Device for the Acutely Failing Heart. The Journal of Thoracic and Cardiovascular Surgery, Nov. 1992, vol. 118, No. 5, pp. 924-929.
Sharony, R. et al. Right heart support during off-pump coronary artery surgery—a multi-center study. Heart Surg Forum. 2002;5(1):13-6.
"Statistical Analysis and Clinical Experience with the Recover® Pump Systems", Impella CardioSystems GmbH, 2 sheets.
Supplementary European Search Report received from the European Patent Office in EP Application No. EP 05799883 dated Mar. 19, 2010, 3 pages.
Takagaki et al. A Novel Miniature Ventricular Assist Device for Hemodynamic Support. ASAIO Journal 2001, pp. 412-416.
Verkerke, Gijsbertus et al., Numerical Simulation of the Pulsating Catheter Pump: A Left Ventricular Assist Device, Artificial Organs 23(10): 924-31; 1999.
Verkerke, Bart et al., The PUCA Pump: A Left Ventricular Assist Device, Artificial Organs 17(5): 365-68; 1993.
Verkerke, CJ et al., Numerical Simulation of the PUCA Pump, A Left Ventricular Assist Device, Abstracts of the XIXth ESAO Congress, The International Journal of Artificial Organs 15(9): 543; 1992.
Wampler, Richard. K., et al., The Sternotomy Hemopump, A Second Generation Intraarterial Ventricular Assist Device; Johnson and Johnson Interventional Systems, PP M218-M220, 223, 1993.
Written Opinion received in PCT Application No. PCT/US2003/04853, dated Feb. 25, 2004, 5 pages.

* cited by examiner

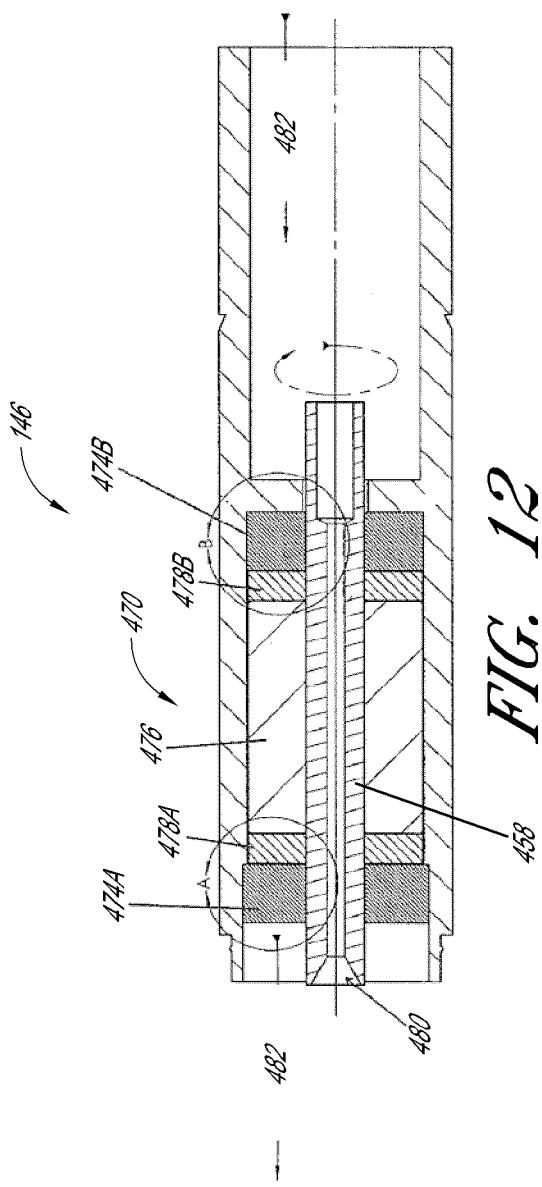
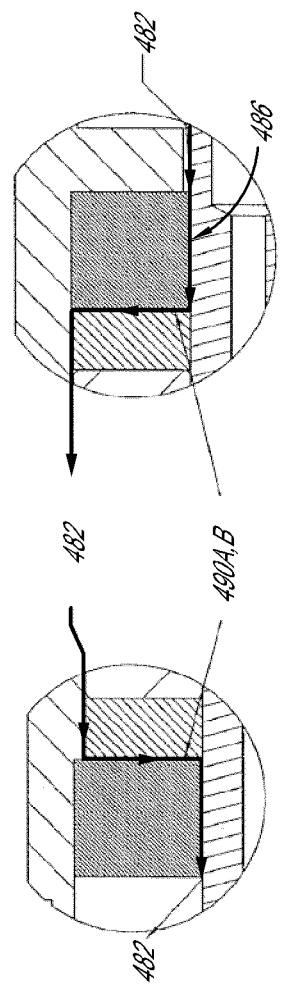
FIG. 12
FIG. 12A
FIG. 12B

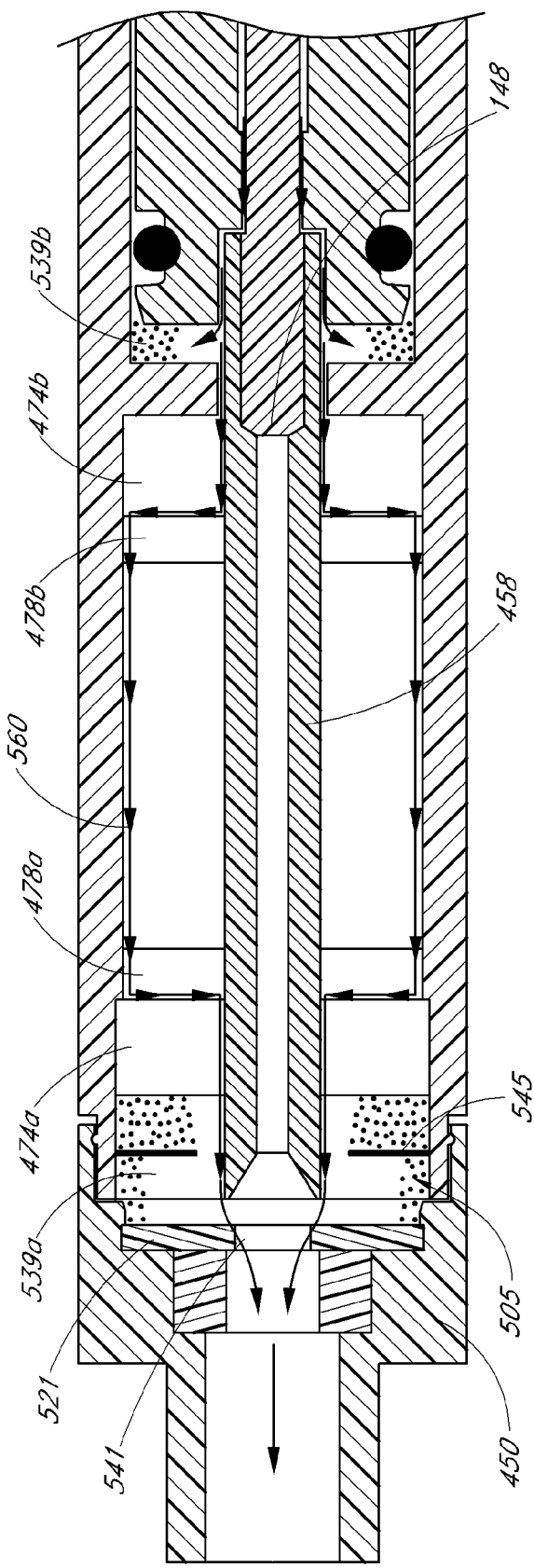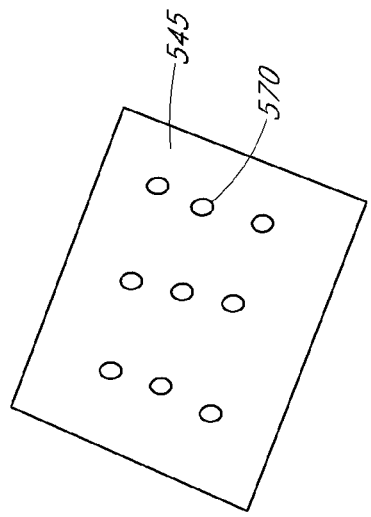
FIG. 15A
FIG. 15B

CATHETER PUMP

CROSS-REFERENCE TO RELATED APPLICATIONS

This application claims priority to U.S. Provisional Application Ser. No. 61/430,171 filed Jan. 6, 2011 entitled Percutaneous Heart Pump, and U.S. Provisional Application Ser. No. 61/430,517 filed Jan. 6, 2011 entitled Percutaneous Heart Pump, both of which are hereby incorporated by reference herein for all purposes.

BACKGROUND OF THE INVENTION

1. Field of the Invention

This application is directed to heart pumps that can be applied percutaneously.

2. Description of the Related Art

Heart disease is a major health problem that claims many lives per year. After a heart attack, only a small number of patients can be treated with medicines or other non-invasive treatment. However, a significant number of patients can recover from a heart attack or cardiogenic shock if provided with mechanical circulatory support.

In a conventional approach, a blood pump having a fixed cross-section is surgically inserted a heart chamber, such as into the left ventricle of the heart and the aortic arch to assist the pumping function of the heart. Other known applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. Surgical insertion, however, can cause additional serious stresses in heart failure patients.

Percutaneous insertion of a left ventricular assist device ("LVAD"), a right ventricular assist device ("RVAD") or in some cases a system for both sides of the heart (sometimes called a "bi-VAD") therefore is desired. Conventional fixed cross-section ventricular assist devices designed to provide near full heart flow rate are too large to be advanced percutaneously, e.g., through the femoral artery. There is an urgent need for a pumping device that can be inserted percutaneous and also provide full cardiac rate flows of the left, right, or both the left and right sides of the heart when called for.

SUMMARY OF THE INVENTION

Various systems, devices and methods are provided relating to a heart pump. In some embodiments, a heart pump is provided comprising a catheter assembly comprising a proximal end, a distal end, and an elongate body extending therebetween. The heart pump further includes an impeller disposed at a distal portion of the heart pump and an infusant flow channel disposed within the catheter assembly for directing infusant through the catheter assembly. At least one debris capturing structure including an edge is positioned along the infusant flow channel.

In some embodiments, a heart pump is provided comprising an elongate catheter body, an impeller disposed at the distal end of the elongate catheter body, and one or more bearings positioned between the catheter body and the impeller, wherein at least one of the bearings comprises a surface facing a portion of the impeller. The heart pump further includes an inflow channel disposed within the elongate catheter body for directing infusant to the surface of the bearings facing the impeller and an outflow channel for directing infusant away from the surface of the bearings. At least one debris capturing structure is positioned along the outflow channel downstream of the one or more bearings.

In some embodiments, a heart pump is provided comprising an elongate catheter body; an impeller disposed at the distal end of the elongate catheter body; one or more bearings positioned between the catheter body and the impeller; a fluid supply line for delivering infusant into the catheter; a fluid return line for transporting infusant out of the catheter; and an infusion system comprising a pump assembly for regulating the infusant flow along the fluid supply line and fluid return line.

In some embodiments, a heart pump is provided comprising an elongate catheter body; an impeller disposed at the distal end of the elongate catheter body; one or more bearings positioned between the catheter body and the impeller; an infusant delivery flow path for delivering infusant into the catheter body; an infusant return flow path for transporting infusant out of the catheter body; and a pump priming structure comprising a shunt and a valve for regulating flow through the shunt, wherein the shunt is connected between the infusant delivery flow path and the infusant return flow path.

BRIEF DESCRIPTION OF THE DRAWINGS

A more complete appreciation of the subject matter of the present inventions and the various advantages thereof can be realized by reference to the following detailed description, in which reference is made to the accompanying drawings in which:

FIGS. 9A, 9B-1, 9B-2; 10 and 10A illustrate details of further embodiments of impeller blade.

FIGS. 12, 12A, and 12B are cross-section views similar to that of FIG. 11, illustrating an infusant outflow path;

FIG. 15A is a cross-sectional view of a proximal end of the catheter assembly including debris capturing structures with baffles.

FIG. 15B is a front view of a baffle having apertures.

A more detailed description of various embodiments of components for heart pumps useful to treat patients experiencing cardiac stress, including acute heart failure, are set forth below.

DETAILED DESCRIPTION

Major components of heart pumps that can be applied percutaneously to a patient are described below in Section I. Section II describes various structures that facilitate the rotatable support of a cantilevered impeller. Section III describes strategies for minimizing a patient's negative reaction to the presence of the systems within the cardiovascular system. Section IV describes various structures that facilitate the capture of debris within the pump. Section V describes an active pump system for maintaining desired flow or pressure. Section VI describes a valve arrangement to expel air and prime the heart pump. Section VII describes various methods and techniques in connection with structures of heart pumps.

I. Overview of Heart Pumps

Figure 1:
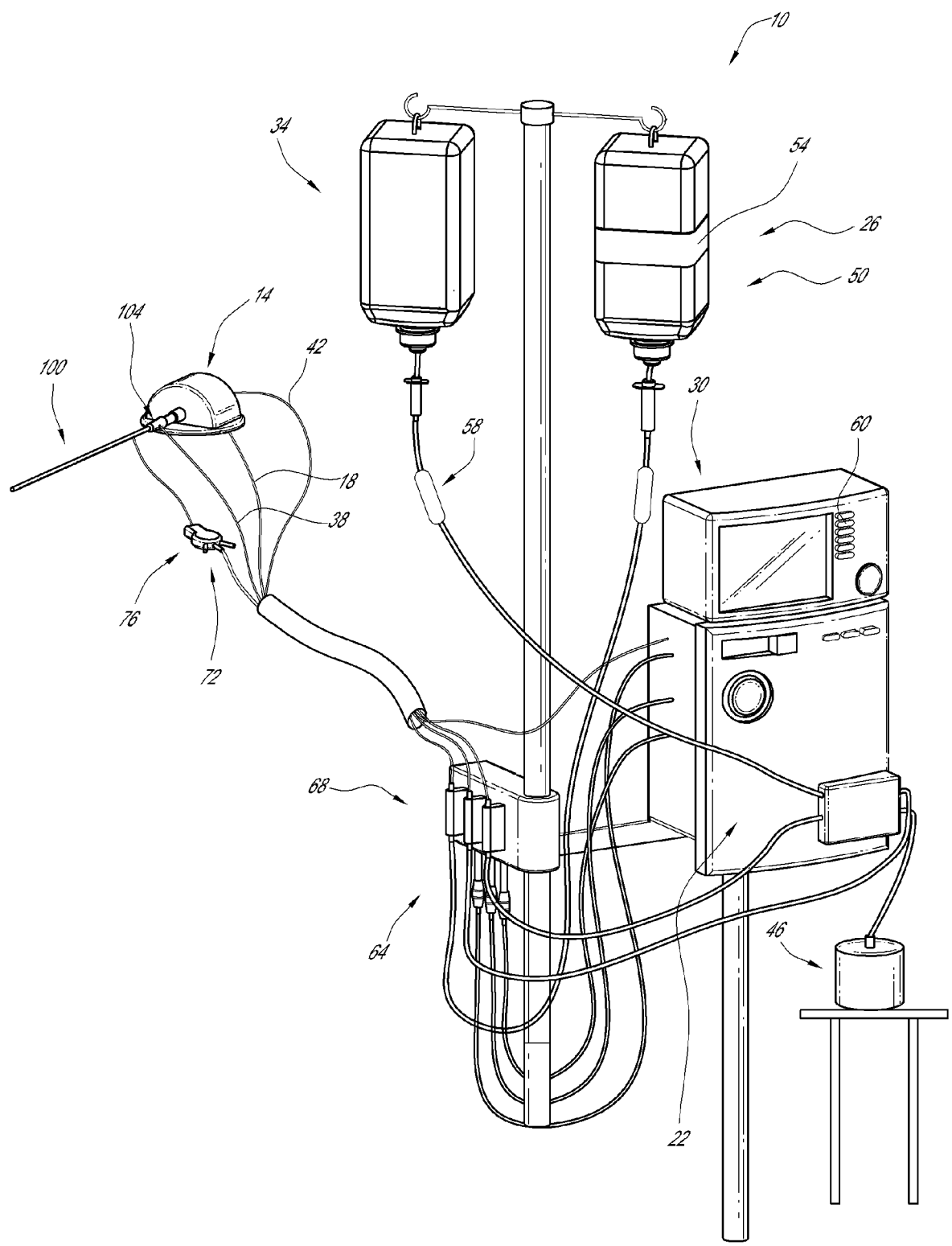
FIG. 1 illustrates one embodiment of a heart pump configured for percutaneous application and operation.

FIG. 1 illustrates one embodiment of a heart pump 10 that includes a catheter assembly 100 having a proximal end 104 adapted to connect to a motor 14 and a distal end 108 (see FIG. 1A) adapted to be inserted percutaneously into a patient. The motor 14 is connected by a signal line 18 to a control module 22 that provides power and/or control signals to the motor 14. As discussed further below, the heart pump 10 may have an infusion system 26 and a patient monitoring system 30.

The infusion system 26 can provide a number of benefits to the heart pump 10, some of which are discussed below in Section V. In one embodiment, the infusion system 26 includes a source of infusant 34, a fluid conduit 38 extending from the infusant source 34 to the proximal end 104 of the catheter assembly 100 and a fluid conduit 42 extending from the proximal end of the catheter assembly 100 to a waste container 46. The flow of infusant to and from the catheter assembly 100 can be by any means, including a gravity system or one or more pumps. In the illustrated embodiment, the infusant source 34 includes an elevated container 50, which may be saline or another infusant as discussed below. Flow from the elevated container 50 can be regulated by a pressure cuff 54 to elevate the pressure of the fluid in the container 50 to increase flow or by a pinch valve 58 or by other means.

The patient monitoring system 30 can be used to monitor the operation of the patient and/or the pump 10. For example, the patient monitoring system 30 can include a user interface 60 coupled with a source of data 64. The data source 64 can include one or more patient conditions sensors, such as pressure sensors 68 that are in pressure communication with the patient and/or operating components within the patient. In one embodiment, the pressure sensors 68 fluidly communicate by a conduit 72 that extends between the sensors and a proximal portion of the catheter assembly 100. The conduit 72 can include a plurality of separable segments and can include a valve 76 to enable or disable the pressure communication to the sensors 68.

The heart pump 10 is adapted to provide an acute or other short-term treatment. A short-term treatment can be for less than a day or up to several days or weeks in some cases. With certain configurations the pump 10 can be used for a month or more.

The catheter assembly 100 extends between the proximal end 104 and the distal end 108. An impeller assembly 116 disposed at the distal end 108 is configured to pump blood to convey blood from one body cavity to another. In one arrangement, the impeller assembly 116 conveys blood proximally through or along a portion of the catheter assembly 100 to provide assistance to the left ventricle of the heart. In another embodiment, the impeller assembly 116 conveys blood distally through or along a portion of the catheter assembly 100 to provide assistance to the right ventricle of the heart. The heart pump 10 is useful as a heart assist device for treating patients with acute heart failure or other heart maladies. The heart pump 10 also can be used in connection with a surgical treatment to support the patient without providing full cardiovascular bypass. A patient could be supported on the device for longer term with proper controls and design.

The catheter assembly 100 is provided with a low profile configuration for percutaneous insertion. For example, the distal end 108 of the catheter assembly 100 can be configured to have an 11 French (3.5 mm) size in a first configuration for insertion and an expanded configuration, such as up to about 21 French (7 mm), once positioned in the body. The larger size facilitates greater flow rates by the impeller assembly 116 as discussed below.

The catheter assembly 100 is configured to enable the distal end 108 to reach a heart chamber after being inserted initially into a peripheral vessel. For example, the catheter assembly 100 can have a suitable length to reach the left ventricle and sufficient pushability and torquability to traverse the intervening vasculature. The catheter assembly 100 may include a multilumen catheter body 120 that is arranged to facilitate delivery and operation of the impeller assembly 116. Further details concerning various embodiments of the catheter body 120 are discussed below in connection with FIGS. 7-7C.

A drive system is provided to drive an impeller within the impeller assembly 116. The drive system includes a motor 14 and a suitably configured drive controller (not shown). The motor 14 may be configured to be disposed outside the patient, e.g., adjacent to the proximal end 104 of the catheter assembly 100. In one advantageous embodiment, the drive system employs a magnetic drive arrangement. The motor 14 is arranged to generate magnetic fields that will be sensed by permanent magnets disposed within the proximal end 104 of the catheter assembly 100. This arrangement facilitates very efficient generation of torque used to drive the impeller assembly 116, as discussed below.

Some embodiments described herein could be incorporated into a system in which a motor is miniaturized sufficiently to be inserted into the patient in use, including into the vasculature. Such an embodiment could be operated by disposing control signal lines within the proximal portion of the catheter body 120. Also, it may be useful to provide the capability to measure blood pressure at the distal end 108 using a device disposed at the proximal end 104. For example, a pressure sensor at the distal end can communicate with a device outside the patient through a lumen of the catheter body 120. Various details of these optional features are described in U.S. Pat. No. 7,070,555, which is incorporate by reference herein in its entirety for all purposes.

In another embodiment, a mechanical interface can be provided between the motor and the proximal end 104 of the catheter assembly 100. The mechanical interface can be between the motor 14 and a drive shaft positioned at the proximal end of the catheter assembly 100.

Figure 11:
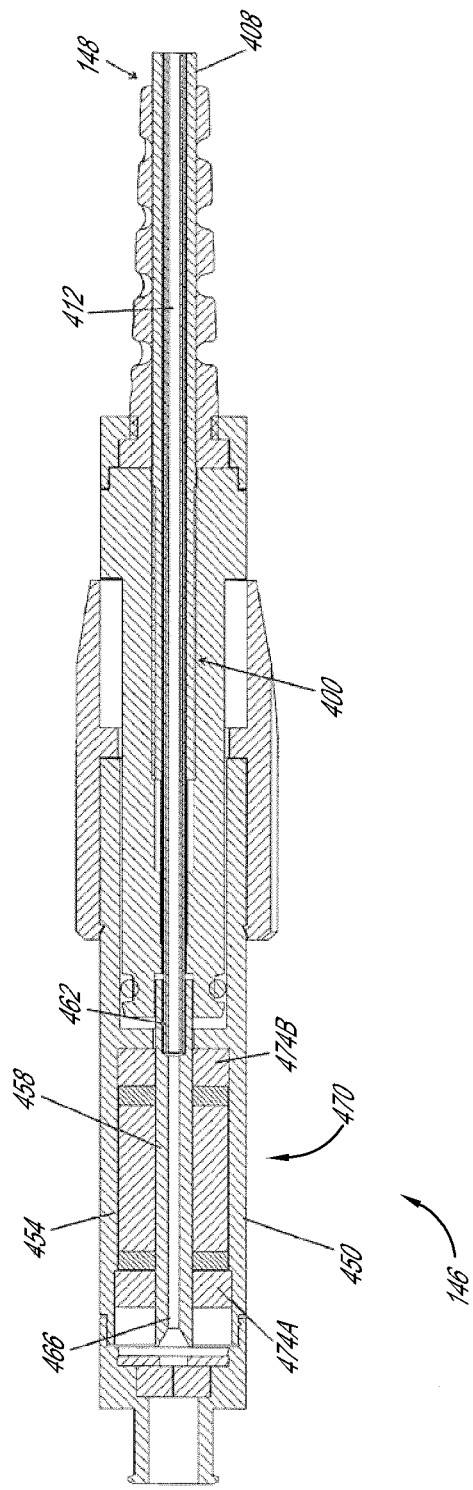
FIG. 11 is a cross-sectional view of a proximal portion of the catheter assembly, taken through the section plane 11-11 on FIG. 1A.

A torque coupling system 140 is provided for transferring torque generated by the drive system to the impeller assembly 116. The torque coupling system 140 is discussed further in Section II(C), but in general can include magnetic interface between the motor 14 and a drive assembly 146 disposed at the proximal end 104 of the catheter assembly 100. The drive assembly 146 is coupled with a proximal end of an elongate drive shaft 148 in one embodiment. The drive shaft 148 extends between the drive assembly 146 and the impeller assembly 116. A distal portion of the drive shaft 148 is coupled with the impeller assembly 116 as discussed below in connection with one embodiment illustrated in FIGS. 4A and 4B. FIG. 11 shows one manner of coupling the proximal end of the drive shaft 148 with the drive assembly 146.

Figure 1A:
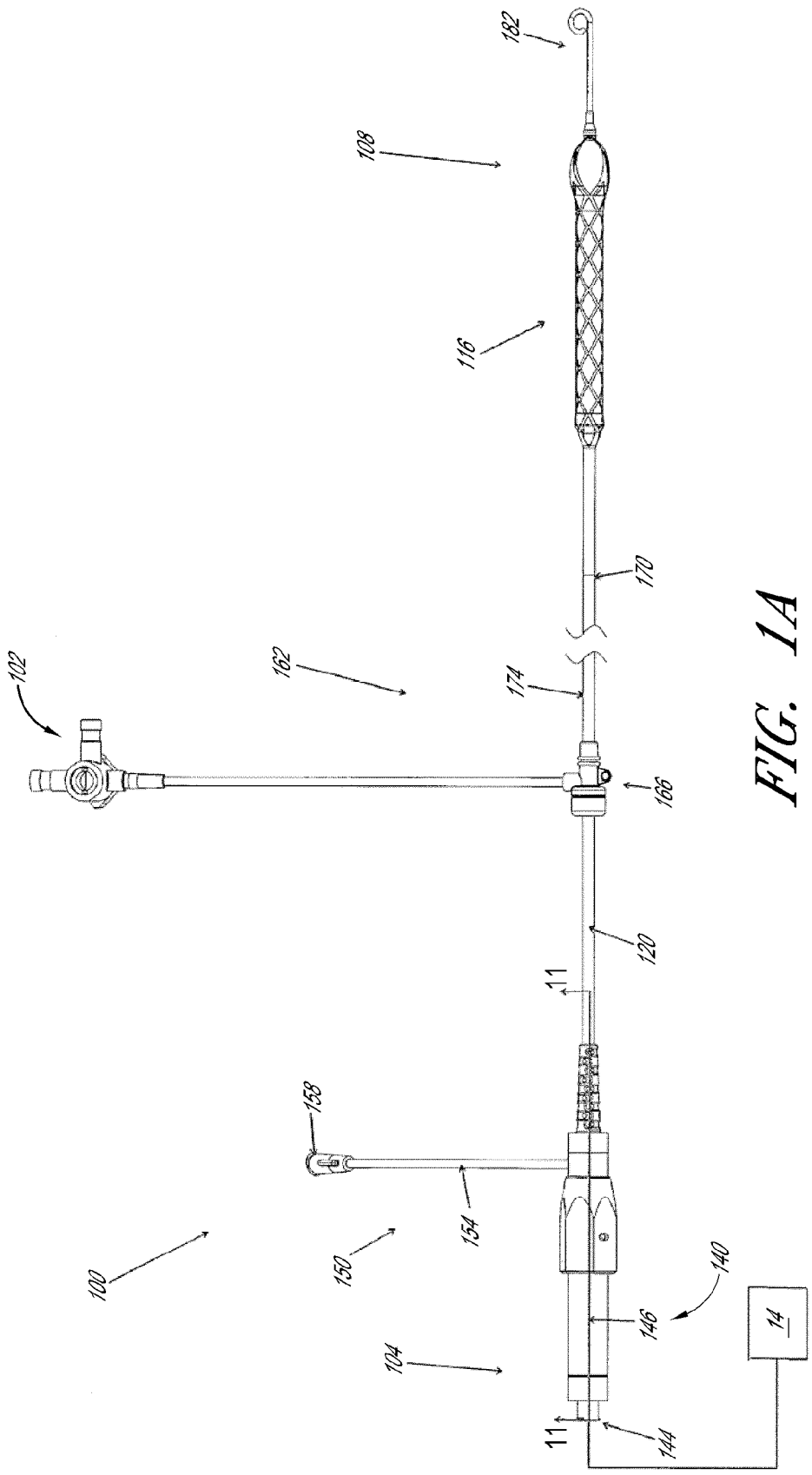
FIG. 1A is a plan view of one embodiment of a catheter assembly adapted to be used with the heart pump of FIG. 1.

As discussed above, the heart pump 10 may also include an infusion system 26. FIG. 1A shows that the infusion system 26 can include an infusion inflow assembly 150 provided adjacent to the proximal end 104 in one embodiment. The infusion assembly 150 can be one component of an infusion system that is configured to convey one or more fluids within the catheter assembly 100. The fluids can be conveyed distally within the catheter assembly 100, e.g., within the catheter body 120, to facilitate operation of the impeller assembly 116, some aspect of a treatment, or both. In one embodiment, the infusion system is configured to convey a lubricant, which can be saline, glucose, lactated Ringer's solution, acetated Ringer's solution, Hartmann's solution (a.k.a. compound sodium lactate), and D5W dextrose solution. In another embodiment, the infusion system is configured to convey a medication, or a substance that both acts as lubricant and medication. As sometimes used herein "infusant" is intended to be a broad term that includes any fluid or other matter that provides performance enhancement of a component of the heart pump 10 or therapeutic benefit, and can be wholly or partly extracted from the system during or after operation of the pump.

In one embodiment, the infusion inflow assembly 150 includes a catheter body 154 having a luer or other suitable connector 158 disposed at a proximal end thererof and an inflow port in fluid communication with one or more lumens within the catheter assembly 100. A lumen extending through the catheter body 154 is adapted to be fluidly coupled with a fluid source connected to the connector 158 to deliver the fluid into the catheter assembly 100 and through one or more flow paths as discussed below in connection with FIGS. 4A, 4B, and 7-7B.

FIGS. 1A and 12 show that the catheter assembly 100 may also include an outlet positioned at a location that is outside the patient when the heart pump 10 is in use to allow infusant to be removed from the pump and from the patient during or after the treatment. The outlet can be fluidly coupled with an infusant return flow path in the catheter body 120 through a fluid port 144 disposed at the proximal end 104.

The catheter assembly 100 can also include a sheath assembly 162 configured to constrain the impeller assembly 116 in a low profile configuration in a first state and to permit the impeller assembly 116 to expand to the enlarged configuration in a second state. The sheath assembly 162 has a proximal end 166, a distal end 170, and an elongate body 174 extending therebetween. In one embodiment, the elongate body 174 has a lumen extending between the proximal and distal ends 166, 170, the lumen being configured to be slidably disposed over the catheter body 120. The arrangement permits the sheath assembly 162 to be actuated between an advanced position and a retracted position. The retracted position is one example of a second state enabling the impeller assembly 116 to expand to an enlarged configuration. The advanced position is one example of a first state that enables the impeller assembly 116 to be collapsed to the low profile configuration. In some embodiments, a luer 102 or other suitable connector is in fluid communication with the proximal end 166 of the sheath assembly 162. The luer 102 can be configured to deliver fluids to the catheter assembly 100, such as priming fluid, infusant, or any other suitable fluid.

Figure 4A:
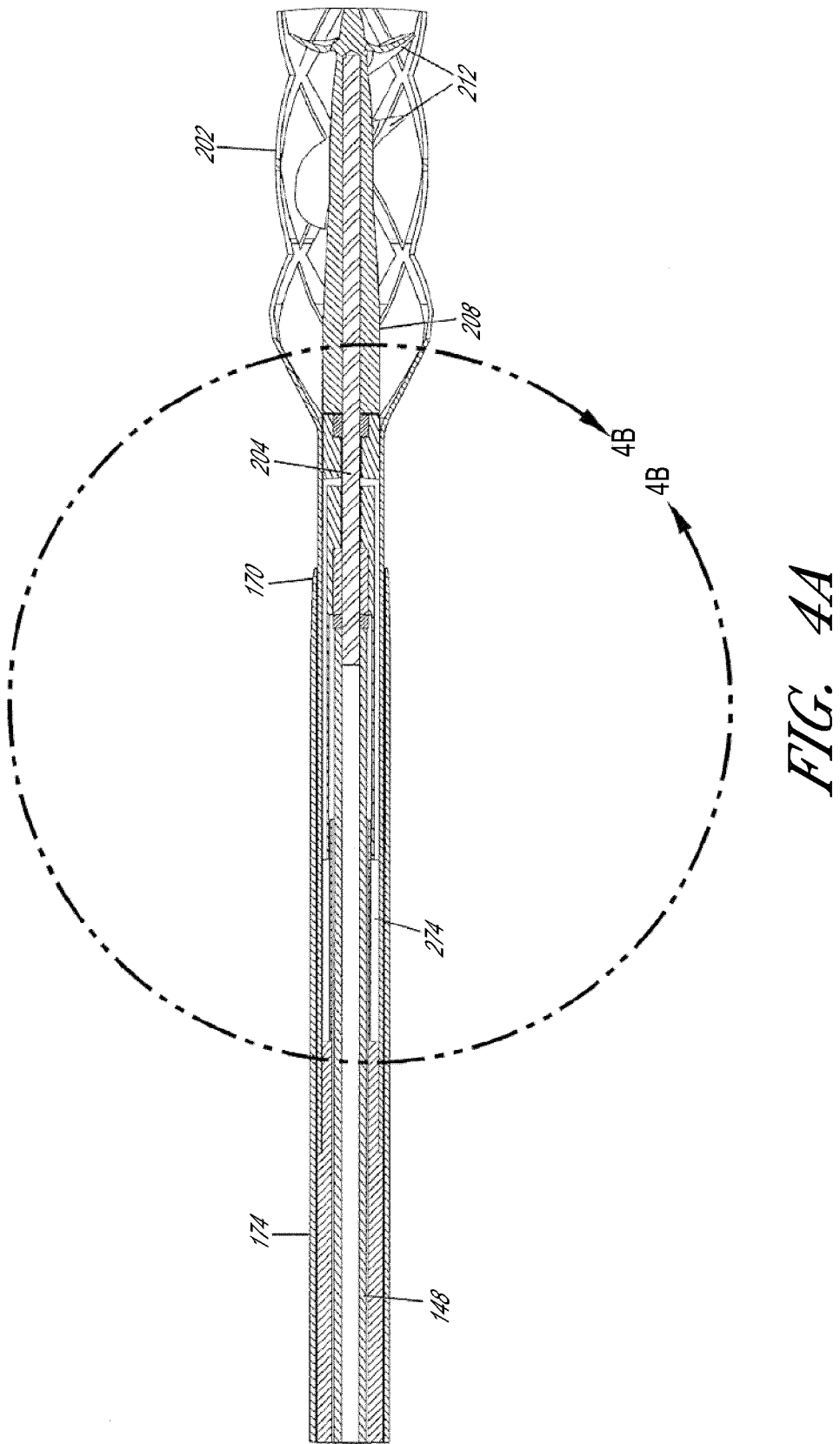
FIG. 4A is a cross-sectional view of a distal portion of the catheter assembly, taken through the section plane 4A-4A shown in FIG. 2.
Figure 4B:
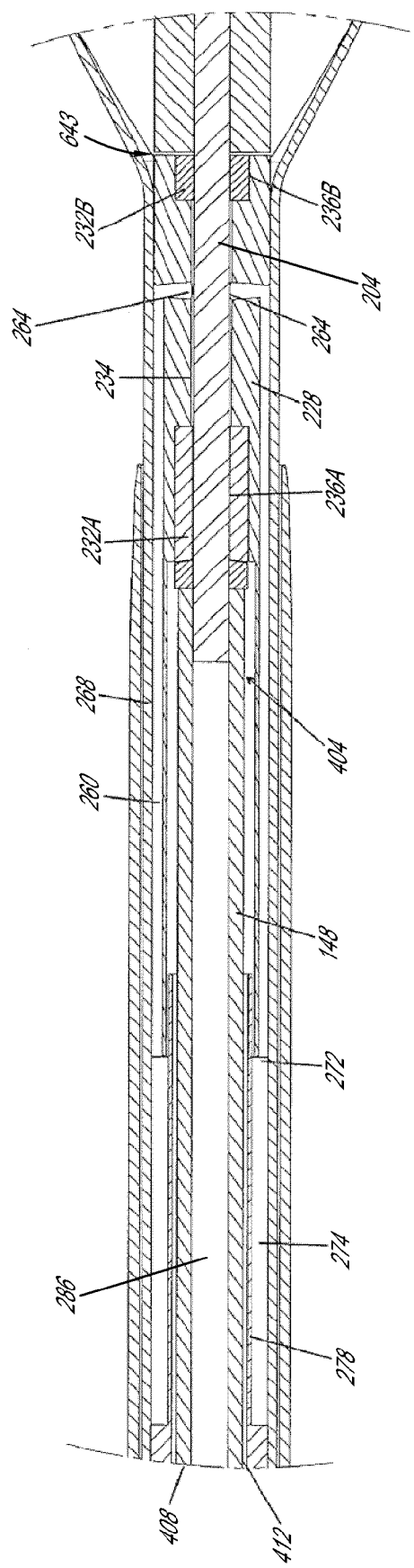
FIG. 4B is a detail view of the distal portion of the catheter assembly, taken at 4B-4B shown in FIG. 4A.

FIG. 1A illustrates a retracted position, in which the distal end 170 of the elongate body 174 is at a position proximal of the impeller assembly 116. In an advanced position, the distal end 170 of the elongate body 174 is positioned distal of at least a portion of the impeller assembly 116. The sheath assembly 162 can be configured such that distal advancement of the distal end 170 over the impeller assembly 116 actuates the impeller assembly 116 from an enlarged state to a more compact state (or low profile configuration), e.g., causing a change from the second state to the first state, as discussed above. Although shown in FIGS. 4A & 4B as a single layer, the elongate body 174 can include a multilayer construction FIGS. 4A & 4B show the elongate body 174 as a single layer structure from the inner surface to the outer surface thereof. In another embodiment, the elongate body 174 has a multilayer construction. In one arrangement, the elongate body 174 has a first layer that is exposed to the catheter body 120 and a second layer exposed that corresponds to an outer surface of the catheter assembly 100. A third layer can be disposed between the first and second layers to reinforce the elongate body 174, particularly adjacent to the distal end thereof to facilitate collapse of the impeller assembly 116. In another construction, a reinforcing structure can be embedded in an otherwise continuous tubular structure forming the elongate body 174. For example, in some embodiments, the elongate body 174 can be reinforced with a metallic coil.

Figure 2:
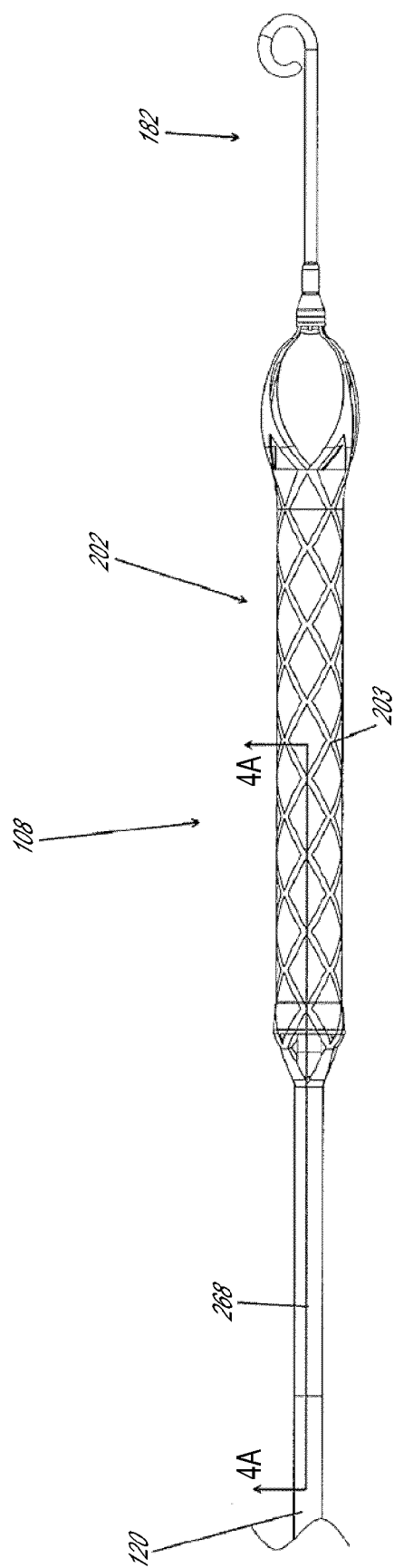
FIG. 2 is a detail view of a distal portion of the catheter assembly illustrated in FIG. 1A.

FIG. 2 show that an impeller housing 202 is disposed at the distal end 108. The impeller housing 202 can be considered part of the impeller assembly 116 in that it houses an impeller and provides clearance between the impeller and the anatomy to prevent any harmful interactions therebetween. The housing 202 and the impeller are also carefully integrated to maintain an appropriate flow regime, e.g., from distal to proximal or from proximal to distal within the housing.

FIGS. 1A and 2 also show that the distal end 108 of the catheter assembly 100 includes an atraumatic tip 182 disposed distal of the impeller assembly 116 in one embodiment. FIG. 1A shows that the atraumatic tip 182 can have an arcuate configuration such that interactions with the vasculature are minimally traumatic. The tip 182 can also be configured as a positioning member. In particular, the tip 182 can be rigid enough to help in positioning the impeller assembly 116 relative to the anatomy. In one embodiment, the tip 182 is rigid enough that when it is urged against a heart structure such as the ventricle wall, a tactile feedback is provided to the clinician indicating that the impeller assembly 182 is properly positioned against the heart structure.

II. Impeller Rotation and Support

The impeller assembly 116 can take any suitable form, but may include an impeller 200 adapted to move a fluid such as blood from an inlet to an outlet of the catheter assembly 100. In certain embodiments the impeller 200 can be cantilevered or otherwise supported for rotation primarily at one end.

Figure 3:
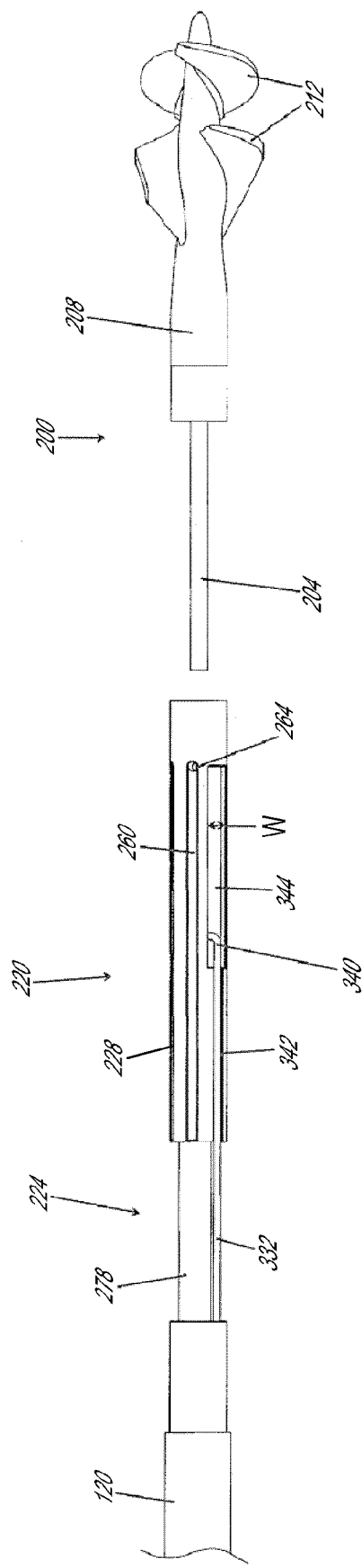
FIG. 3 is an exploded view of a portion of an impeller assembly of the catheter assembly of FIG. 1A.

FIG. 3 shows that the impeller 200 includes a shaft 204, a central body or hub 208, and one or more blades 212. Particular features of the impeller blades 212 are discussed further below in Section III(A).

Figure 9:
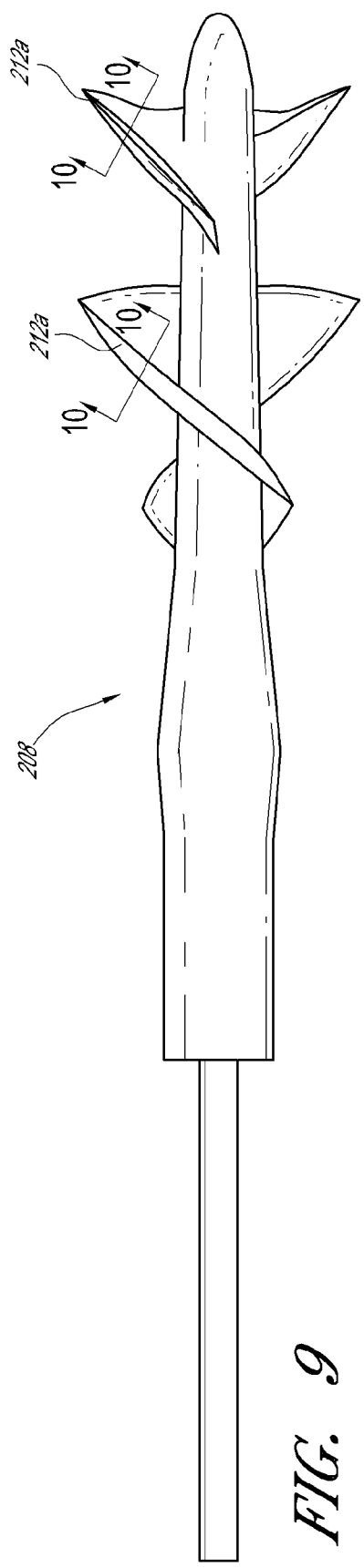
FIG. 9 illustrates one embodiment of an impeller assembly.

The shaft 204 and hub 208 can be joined in any suitable fashion, such as by embedding a distal portion of the shaft within the hub 208. The blades 212 can be spaced out proximal to distal along the axis of the shaft. In some embodiments, the blades 212 are provided in blade rows. FIG. 9 shows that the distal end of the shaft 204 can extend at least to an axial position corresponding to one of the blade rows. In some embodiments, the shaft 204 can be solid. In other embodiments, the shaft 204 has a lumen extending axially through the hub so that a guidewire can be passed through the catheter assembly 100. Details of variations with a lumen are discussed further in U.S. application Ser. No. 12/829,359, filed Jul. 1, 2010, titled BLOOD PUMP WITH EXPANDABLE CANNULA, which is incorporated by reference herein for all purposes and in its entirety.

A. Infusant Delivery and Removal System

The operation and duty cycle of the impeller assembly 116 can be lengthened by providing a hydrodynamic bearing for supporting the shaft 204. A hydrodynamic bearing can be supported by a lubricant, such as isotonic saline, which can be delivered in a continuous flow. The lubricant can be delivered through the infusion system to an outside surface of the shaft 204. The infusant may be directed onto the shaft from a radially outward location. In some arrangements, the lubricant flow is controlled such that a first volume of the lubricant flows proximally along the shaft 204 and a second volume flows distally along the shaft, the first volume being different from the second volume.

FIGS. 3-8 show various structures for providing rotational support of a proximal portion of the shaft 204 within the distal portion of the catheter assembly 100. For example, a bearing assembly 220 can be disposed at a distal end 224 of the multilumen catheter body 120. In one embodiment, the bearing assembly 220 includes a housing 228 and one or more bearings configured to support the proximal portion of the shaft 204. The bearing assembly 224 includes a plurality of bearings 232a, 232b disposed within the bearing housing 228. Various materials that can be used for the bearing are discussed below.

Figure 6:
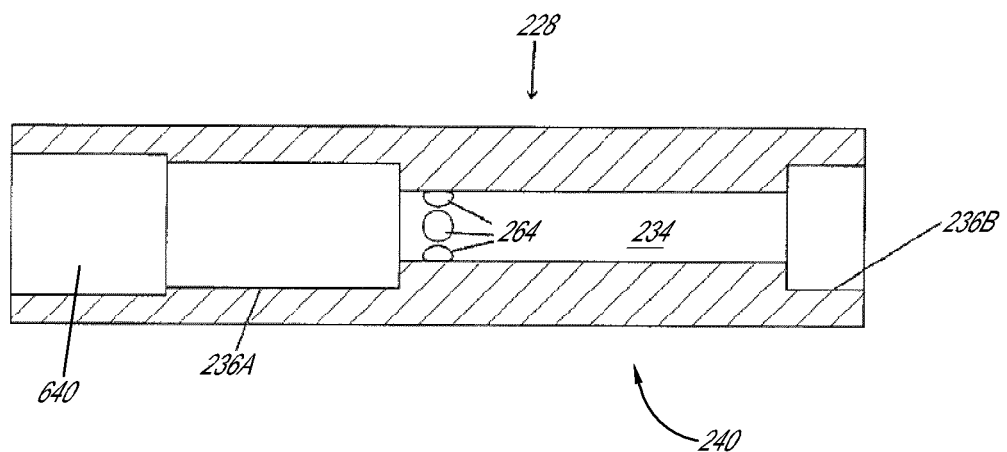
FIG. 6 is a cross-sectional view of a bearing housing of the bearing assembly of FIG. 5.

FIG. 6 shows that the bearing housing 228 has a lumen 234 extending therethrough with a proximal enlarged portion 236a and a distal enlarged portion 236b. The housing 228 comprises a shoulder defining a narrow portion 240 of the lumen 234 disposed between the enlarged portions 236a, 236b. The first and second bearings 232a, 232b can be disposed within the enlarged portions 236a, 236b of the bearing housing 228.

In one arrangement, the proximal end of the shaft 204 (e.g., as shown in FIG. 4A) is received in and extends proximally of the second bearing 232b. In some embodiments there can be one bearing (e.g., only bearing 232a), while in other embodiments both bearings 232a and 232b can be used. In some embodiments, the bearing(s), e.g., bearings 232a and/or 232b, can be friction fit or interference fit onto the impeller shaft 204. Accordingly, the shaft 204 can be supported for rotation by the bearings 232a, 232b as well as in the narrow portion 240 of the housing 228. In embodiments where the bearing(s) 232a, 232b are friction or interference fit onto the shaft, the bearing(s) 232a, 232b can be configured to rotate with the shaft 204 relative to the bearing housing 228. Further, the bearing(s) 232a, 232b can have a relatively large clearance with the bearing housing 228. The clearance between the shaft 204 and the bearing housing 228, at regions that are not coupled with the bearing, can be in the range of about 0.0005 to about 0.001 inch. In certain embodiments, the clearance can be within a larger range, such as at least about 0.0005 inches, about 0.001 inches or up to about 0.005 inches. In embodiments with multiple bearing(s) 232a, 232b, the clearance can be different for the bearings 232a, 232b, such as providing a larger clearance at the proximal bearing 232a.

Figure 5:
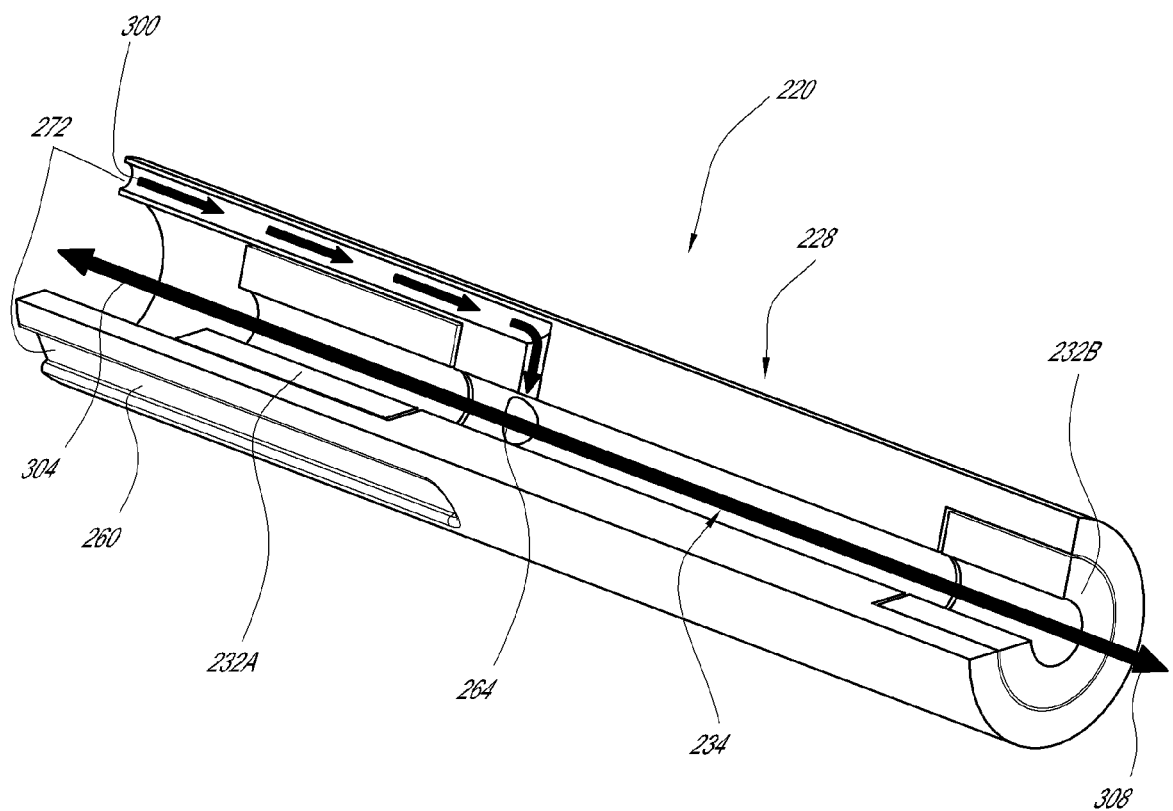
FIG. 5 is a cross-sectional perspective view of a bearing assembly of the catheter assembly of FIG. 1A.

In other embodiments, such as in FIG. 5, the bearing(s) 232a, 232b may not be friction or interference fit onto the shaft 204. In these embodiments, the bearing(s) 232a, 232b may be disposed within the bearing housing 228, for example by an interference or press fit. The shaft 204 may then rotate with respect to the bearing(s) 232a, 232b, and there can be a clearance between the shaft 204 and the bearing(s) 232a, 232b. The clearance between the shaft 204 and the bearings 232a, 232b can be in the range of about 0.0005 to about 0.001 inch. In certain embodiments, the clearance can be within a larger range, such as at least about 0.0005 inches, about 0.001 inches or up to about 0.005 inches. The clearance can be different for the bearings 232a, 232b, such as providing a larger clearance at the proximal bearing 232a. In certain embodiments, the bearing housing 228 may provide a thrust surface for bearing axial loads. In other embodiments, there may be other bearings located either distally or proximally of the bearing housing 228 that are configured to bear axial loads. In other embodiments, the fit between the bearings 232a, 232b and the shaft 204 can be tight, which can also assist in bearing axial loads in some aspects.

At least the proximal portion of the shaft 204 can be made of a material that will not corrode or otherwise be made to be inert when immersed in the lubricant or other infusant. The material may be one that will not corrode in isotonic saline. Suitable materials may include a wide variety of metals, including alloys, and at least saline-resistant stainless steel and nickel-based alloys. Also, the shaft 204 could be made as a composite to include advantageous properties of a plurality of materials. In some cases the shaft 204 could be formed as a polymer. The class of polymers selected would include those that can form a shaft 204 of a certain stiffness suitable in this application. For example, polycarbonate or PEEK could be used. In certain configurations, the polycarbonate, PEEK, or other suitable polymer can provide enhanced performance by being combined with a second material or structure. A glass or carbon filled polycarbonate or other stiff polymer could also be used.

As discussed above, a hydrodynamic bearing between the shaft 204 and the bearings 232a, 232b may be utilized in various embodiments. In one such arrangement, a continuously replenished fluid film is provided at least between the inner wall of the bearing housing and an adjacent moving structure, such as the impeller shaft or an outer surface of a bearing. For example, the bearing housing 228 can be configured to permit a lubricant to be delivered therethrough into the lumen 234. The bearing housing 232 can include a plurality of channels 260 disposed therein extending proximally from a plurality of ports 264 located at the narrow portion 240 of the housing 228. Each port 264 can communicate with one of the channels 260 to provide fluid communication into the lumen 234.

As shown in FIG. 5, the channels 260 can be formed in the wall of the housing 228. In one embodiment, the channels 260 are formed as open depressions, e.g., as flutes, extending along the housing 228. In this embodiment, the channels 260 can be enclosed by a separate structure that is disposed around the housing 228. FIG. 4B shows that a proximal portion 268 of the impeller housing 202 can be sized to tightly fit over the outer surface of the bearing housing 228, enclosing the radially outward portion of the channels 260. In this arrangement, at least a portion of a flow path is formed between an outer surface of the bearing housing 232 and a separate outer sleeve.

Fluid communication between the port 264 in the bearing housing 228 and the infusion inflow assembly 150 can be by any suitable combination of lumens within the catheter assembly 100. For example, in one embodiment, each of the channels 260 has a proximal port 272 that communications with an annular space 274 formed in the catheter assembly 100. The annular space 274 can be formed between a plurality of separate overlaid structures in the catheter assembly 100. FIGS. 4A and 4B show that the annular space 274 is formed between an outer surface 278 of the multilumen catheter body 120 and an inner surface of the proximal length 268 of the housing 202.

Figure 7:
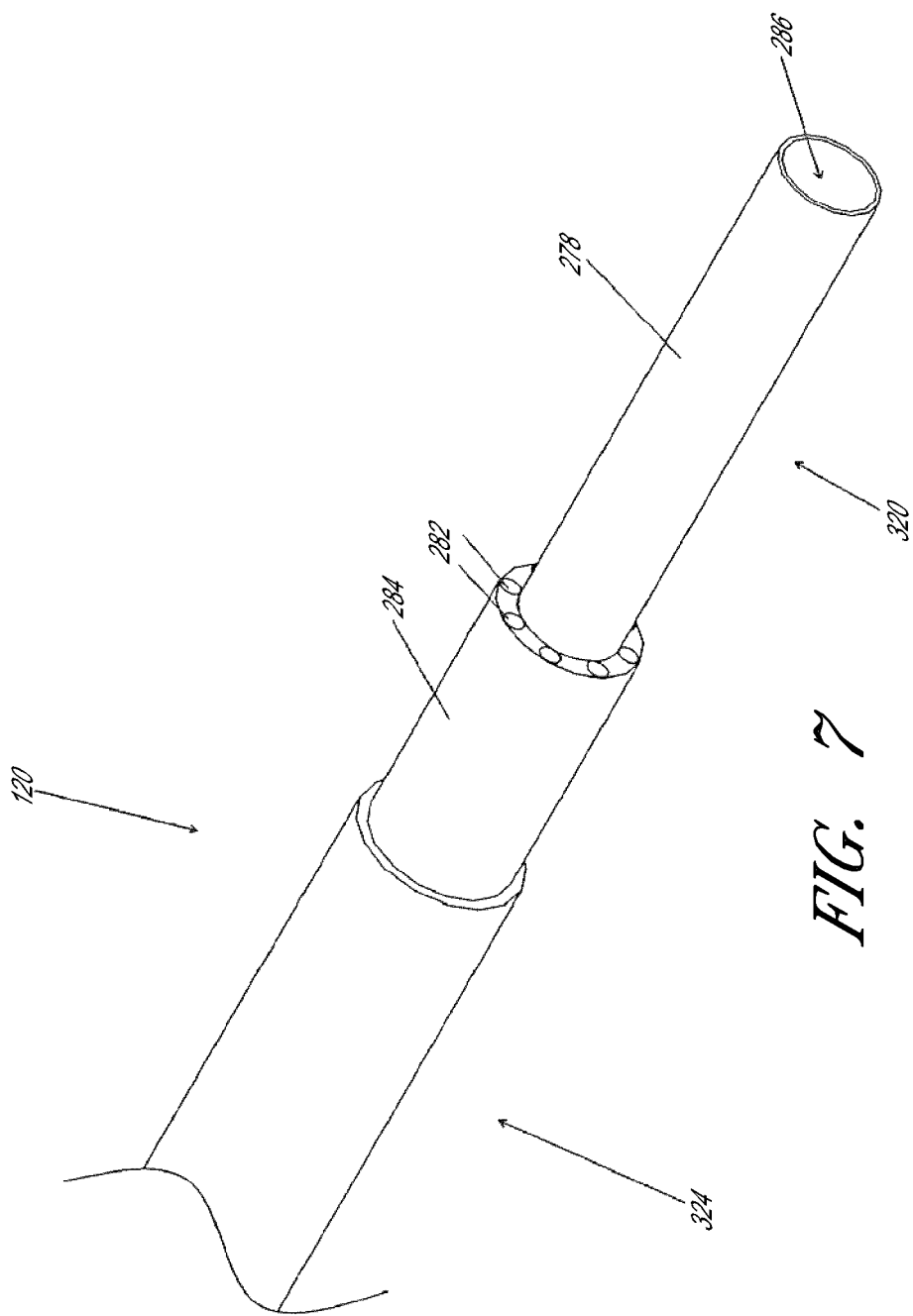
FIG. 7 is a perspective view of one embodiment of a catheter body that can be used to house a drive shaft and to convey an infusant to the bearing housing of FIG. 5.
Figure 7C:
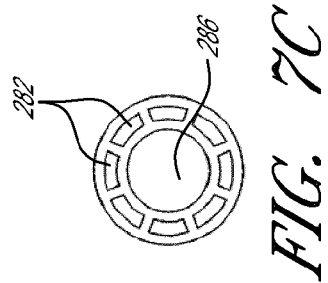
FIGS. 7A-7C show variations of the catheter body of FIG. 7.
Figure 7B:
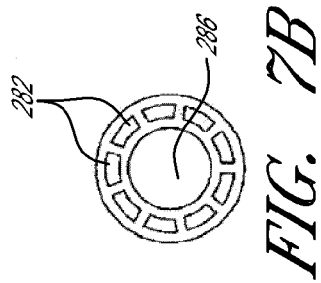
Figure 7A:
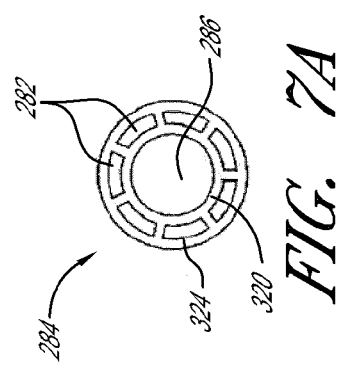

Fluid communication is provided in the catheter assembly 100 between the space 274 and the infusion inflow assembly 150. For example, a plurality of lumens 282 formed in the multi-lumen catheter body 120 can be dispersed circumferentially about the catheter body 120 at a peripheral circumferential region 284, as illustrated in FIGS. 7-7C. The peripheral position of the lumens 282 enables a central area of the catheter body 120 to be dedicated to a central lumen 286. By providing a plurality of smaller lumens 282 located at the periphery, a relatively large flow rate can be delivered through a relatively small circumferential band (when considered in cross-section) of the catheter body 120. Each of the lumen 282 has a distal port 290 that communicates with the space 274.

A proximal portion of the lumens 282 can take any suitable form. For example, the lumens 282 can communicate at their proximal end with a flow diverting structure (not shown) that is in fluid communication with the infusion inflow assembly 150. In some embodiments the lumen 282 can be disposed circumferentially about the central lumen 286. The catheter assembly 100 can include a flow diverting structure or connector, e.g., disposed about the proximal end of the catheter body 120 that is configured to divert the infusant into the lumens 282 for distally directed flow therein. In other embodiments, the catheter assembly 120 can include a flow diverting structure disposed adjacent the distal end thereof that is configured to divert the infusant into the lumens 282 from the central lumen 286 for proximally directed flow in the lumens 282.

FIG. 5 includes arrows that illustrate the flow of infusant into the bearing assembly 220. In one arrangement, the inflow of infusant is indicated by an arrow 300 which is shown pointing distally within one of the channels 260 of the bearing housing 228. The infusant flow enters the bearing housing through the ports 264. Although flow is shown in one channel 260, corresponding flow may be provided in each of a plurality of channels 260 disposed around the central lumen 234. An arrow 304 illustrates that at least a portion of the infusant delivered through the port 264 may flow generally proximally within the bearing housing 228. An arrow 308 illustrates that at least a portion of the infusant delivered through the port 264 may flow generally distally within the bearing housing 228.

FIG. 5 illustrates the arrows 304, 308 as proximally and distally directed, respectively. However, the high speed rotation of the impeller shaft 204 within the housing 228 will create a thin film of lubricant spacing the impeller shaft 204 from the surfaces of the bearings 232a, 232b. This thin film will extend all the way around the shaft 204 and thus each portion of the flow will have a spiral or helical flow direction.

The bearings 232a, 232b can have different configurations to enhance the performance of the pump 10. For example, the proximal bearing 232a can be longer along the longitudinal axis of the bearing housing 228 than the distal bearing 232b. A longer proximal bearing 232a is believed to better control runout of the shaft 204. Better runout control on the shaft 204 is believed to enhance the control of the position of the blades 212 relative to the housing 202. Less runout reduces excessive variation in the gap between the blades 212 and the housing 202, providing biocompatibility benefits such as reduced hemolysis.

In some embodiments, such as those in FIG. 5 where the bearings 232a, 232b are not friction fit or interference fit onto the shaft 204, the distal bearing 232b has a smaller inner diameter than the proximal bearing 232a. If the shaft 204 has a constant diameter, the smaller inner diameter should provide greater control of angular deflection of the shaft. Controlling angular deflection can enhance relative position control of the blades 212 and housing 202, providing blood handling benefits such as reduced hemolysis. A smaller clearance could also be provided by enlarging the diameter of the shaft 204 at the axial position of the distal bearing. In some embodiments, the larger inner diameter of the bearing 232b enables a larger volume of lubricant to flow proximally and a lesser volume to flow distally in the lumen 234.

The continuous introduction of lubricant maintains a constant, predictable and durable rotational bearing state between stationary component, e.g., the bearing housing 282, and a moving component, e.g., the shaft 204, a component of the bearings 232a, 232b, or both the shaft 204 and a component of the bearings 232a, 232b. Also, continuous lubricant inflow provides a means for removing heat generated by the relative motion between the shaft 204 and the bearings. Also, the infusant can create fluid pressure within the catheter assembly 100 that can push debris generated within or by the pump 10 out of the bearing housing 220. Enhancing the volume of infusant that flows along the path indicated by the arrow 304 enhances the likelihood that debris generated by or present in the pump will be removed from the proximal end rather than to be trapped inside the distal portion of the catheter assembly 100.

Another technique for controlling infusant flow in the lumen 234 is to locate the port 264 between the bearings 232a, 232b and closer to one of the bearing. For example, the ports 264 can be located adjacent to the proximal bearing 232a in one embodiment. This provides a shorter path of egress out of the narrow portion 240 of the bearing housing 228 in the proximal direction.

Figure 8:
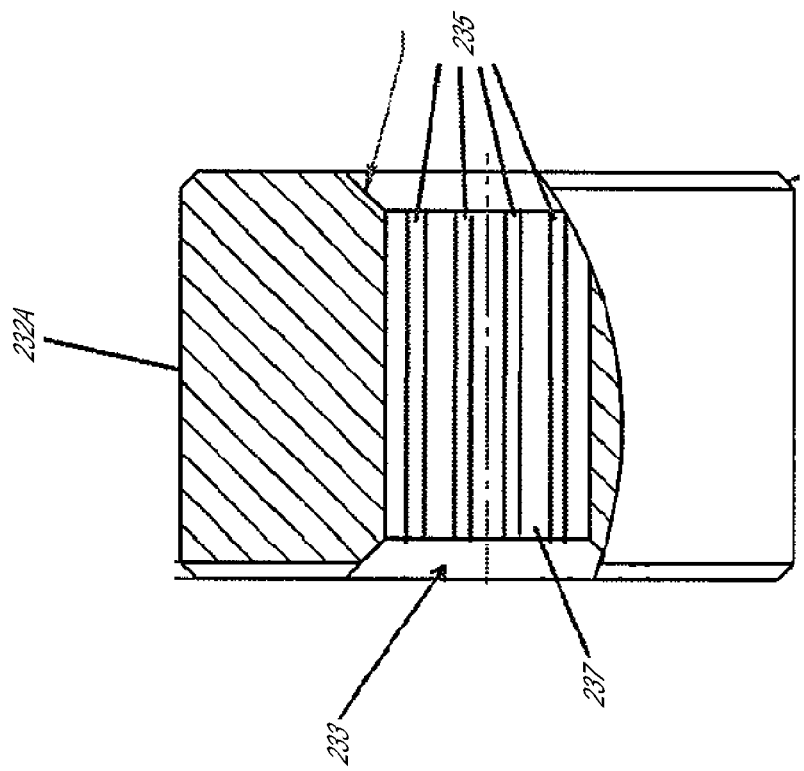
FIG. 8 illustrates a surface configuration of one embodiment of a bearing adapted to enhance or control flow of an infusant in the bearing assembly of FIG. 5.

Other strategies for controlling the flow of infusant within the bearing housing 228 include modifying a surface within one or more of the bearings 232a, 232b. FIG. 8 shows a surface modification 233 provided in a bearing 232a to enhance proximally directed flow. The surface modification 233 comprises a plurality of axially oriented grooves 235 in one embodiment. In another embodiment, the surface modification 233 includes one or more spiral grooves. The spiral grooves can be formed with a groove entrance that is substantially parallel with a flow direction of infusant between the bearings 232a, 232b such that a reduction of velocity of the flow is minimized. In one embodiment, each spiral groove includes at least about 3 turns disposed on the inner surface of the bearing between the proximal and distal ends of the bearing. In another embodiment, each spiral groove has adjacent turns that are spaced apart by a minimum pitch of 0.125 inches (3.2 mm). In another embodiment, each spiral groove has an axial density of about 32 turns per inch (about 1.3 turns per mm). The grooves are formed in the surface 237 of the bearing 232a upon which the impeller shaft 204 is supported. The grooves 235 locally enlarge the clearance between the shaft 204 and the surface 237 so that a greater volume of infusant can flow distal-to-proximal across the bearing 232a. The surface modification 233 reduces back-pressure limiting the distal-to-proximal across the bearing 232a.

In other embodiments, it may be desirable to enhance distally directed flow. For example, the infusant may be provided with a fluid intended to be delivered to the patient. In such embodiments, the surface modification 233 can be provided on the distal bearing 232b. In certain embodiments, both proximal and distal bearings 232a, 232b are provided with flow enhancing modifications to enhance heat transfer or purging of the bearing assembly 220. In such embodiments, one of the bearings may have a greater degree of flow enhancement provided on the bearing surface.

The arrangement of the bearing assembly 220 can be a factor in selecting an appropriate infusant. Saline is one possible infusant, but other sufficiently biocompatible infusants could be used. Other embodiments are configured such that little or no infusant flows out of the pump into the patient. For such embodiments, other infusant fluids can be used, such as glucose.

FIG. 7 illustrates further features of the catheter body 120. The catheter body 120 comprises an inner most portion 320 that defines the central lumen 286. The inner most portion 320 is disposed within, e.g., circumferentially surrounded by, the peripheral circumferential region 284. A continuous outer circumferential region 324 can be provided around the peripheral circumferential region 284 to fully enclose the lumens 282, discussed above. FIGS. 4A and 4B illustrate that a distal end of the inner most portion 320 is configured to be received and secured within a proximal portion of the lumen 234 within the bearing housing 228. FIG. 4B illustrates that a region of overlap can be provided between a distal portion of the inner most portion 320 and a proximal portion of the bearing housing 228. This construction provides a continuous lumen defined in part by the central lumen 286 of the catheter body 120 and in part by the lumen 234 of the bearing housing. As discussed further below, this continuous lumen provides a space for the rotation of the shaft 204 of the impeller assembly 116 and the drive shaft 148 of the torque coupling system 140.

The physical connection between the bearing housing 228 and the catheter body 120 can be achieved in any suitable manner. FIG. 3 illustrates that in one arrangement, a slideable connection is provided. In this arrangement, a rod 332 is provided between the bearing housing 228 and the catheter body 120. The rod 332 can have any suitable configuration, but in various embodiments the rod 332 has a proximal end configured to be received in a recess or lumen formed in the catheter body 120 and a distal end 340 configured to couple with the bearing housing 228. FIG. 3 shows that the distal end 340 of the rod 332 can be configured to engage with a feature of the bearing housing 228 so that a limited range of sliding is permitted.

In one embodiment, the bearing housing 228 has an elongate channel 342 configured to receive a middle portion of the rod 332 and an enlarged depression 344 located at the distal end of the channel 342. The depression 344 has a width that is sufficient to receive a wide distal end of the rod 332. The depression 344 can be configured to have an axial length along the housing 228 that can define a range of motion of the bearing housing 228 relative to the catheter body 120.

In one arrangement, the bearing housing 228 is positioned relative to the catheter body 120 and the rod 332 such that the distal portion of the rod 332 is located at the distal end of the depression 344. Thereafter, the catheter assembly 100 can be manipulated such that the bearing housing 228 moves distally relative to the catheter body 120 and the rod 332 such that the distal portion of the rod 332 is located at the proximal end of the depression 344. In the distal position, the impeller assembly 116 is located more distally than in the proximal position. As discussed further below, this enables a variety of techniques for unfurling the impeller blades 212 within the housing 202.

B. Bearing Configurations

Any suitable bearing can be used in the catheter assembly 100. The provision of an infusant for hydrodynamic support enables a wide range of bearing materials to be used. If saline or other more corrosive infusant is used, the bearing must be carefully configured to not degrade within the expected duty cycle of the pump 10. Some polymeric materials are advantageously not degraded by isotonic saline, and are acceptable materials from this perspective. Under the fluid-dynamic conditions, a hydrodynamic bearing that is supported by a biocompatible infusant such as isotonic saline may be used in some embodiments. It is believed that certain polymer bearings in combination with isotonic saline can support such conditions as 35,000-50,000 psi-ft/min for an appropriate duty cycle. Other aspects that can guide the choice of bearing configurations include minimizing thermal expansion, given the heat that could be generated in the heart pump 10, and minimizing moisture absorption.

Any suitable polymeric material may be used for the bearings 232a, 232b. The polymeric material can include a homopolymer, a copolymer, or a mixture of polymers. The polymeric material can include thermoplastic or thermoset polymers. Examples of polymers that can be used for bearings 232a, 232b include, but are not limited to, one or more of a polyketone, a polyether, a polyacetal, a polyamide-imide, a polyacetal, polyether ether ketone (PEEK), polytetrafluoroethylene (PTFE), and polyphenylene sulfide (PPS).

The polymeric material can also include (e.g., can be mixed, combined, and/or filled with) one or more additives such as a reinforcer and a lubricant. Specific additives include, but are not limited to, graphite, carbon fiber, glass fiber, and PTFE. Those of ordinary skill in the art may appreciate that the additives may be polymeric or non-polymeric. In some embodiments, the polymeric material used for bearings 232a and/or 232b can include PEEK, carbon fiber, PTFE, and graphite. In other embodiments, the polymeric material can include PPS and glass fiber. In yet other embodiments, the polymeric material can include a polyamide-imide polymer, carbon fiber, and graphite. The polymeric material can include any suitable amount of additive(s). For example, the polymeric material can include a total amount of additive(s) in the range of from about 1 wt % to about 50 wt %, based on the total weight of the polymeric material. In other embodiments, the polymeric material used for bearings 232a, 232b may not include any additives.

The polymeric material chosen for bearings 232a, 232b can have particular characteristics that advantageously affect the performance of the bearings. For example, in order to minimize thermal expansion caused by the heat generated in the heart pump 10, a preferred material would be subject to a minimum of dimensional change, and can have a coefficient of thermal expansion in the range of from about $1.2 \times 10^{-5}$ °F.$^{-1}$ to about $25.2 \times 10^{-5}$ °F.$^{-1}$. In other embodiments, the polymer used for bearings 232a, 232b has a coefficient of friction in the range of from about 0.15 to about 0.3. In another example, in order to minimize or prevent water absorption, the selected polymeric material can have a water adsorption in the range of from about 0.01% to about 0.4% over a 24 hour period. In yet another example, the polymeric material can be suitable for high pressure and velocity performance, and can have a limiting pressure-velocity (PV) in the range of from about 20,000 psi-ft/min to about 50,000 psi-ft/min.

The polymeric material used for bearings 232a, 232b may be commercially available. Examples of suitable, commercially-available polymeric materials include, but are not limited to, Ketron PEEK-HPV, Turcite A, Turcite X, Turcite TX, Rulon LR, Rulon J, Rulon 641, Rulon AR, Techtron HPV PPS, Ryton PPS, Torlon 4301, and Torlon 4501. In some embodiments, the polymeric material used for bearings 232a, 232b is Ketron PEEK-HPV.

Of course, other bearing configurations and/or materials would be suitable under other conditions, e.g., with less corrosive infusants or if a hydrostatic or non-hydraulic bearing is used.

C. Torque Coupling Systems

A torque coupling system is provided to rotate the impeller 200 at a high rate to move blood from inside a heart camber to a location within a patient's vasculature in amounts sufficient to sustain the patient or provide treatment to the patient. The torque coupling system couples the impeller 200 with the motor 14, which may be disposed outside the patient. It is expected that the impeller 200 and the drive shaft 148 are to be rotated at 25,000-30,000 revolutions per minute for a period of seven to ten days. To provide reliable performance under these conditions, isotonic saline or other lubricant is provided between the draft shaft 148 and stationary components therearound.

FIGS. 11 and 4B illustrate proximal and distal portions 400, 404 of the drive shaft 148. The proximal portion 400 is coupled with the drive assembly 146 such that rotation of the drive assembly 146 rotates the drive shaft 148. The distal portion 404 of drive shaft 148 is coupled with the impeller shaft 204 such that rotation of the drive shaft 148 causes rotation of the impeller shaft 204. The drive shaft 148 also includes an elongate body 408 that extends between the proximal and distal portions 400, 404. The elongate portion 408 comprises a lumen 412 extending therethrough.

The size of the elongate body 408 may be as small as possible to minimize the cross-sectional profile of the catheter assembly 100. The cross-sectional profile of the catheter assembly 100 corresponds to the crossing profile of the catheter assembly, which limits where the system can be inserted into the vasculature. The lumen 412 is sized to permit a guidewire to be advanced therethrough in some embodiments. The use of a guidewire is optional, but may simplify insertion.

In one embodiment, the elongate body 408 comprises a multi-layer construction. In some embodiments, each layer can include at least one coil wire or a plurality of coil wires all wound in a same orientation. For example, a two-layer, counter-wound wire construction is particularly advantageous. A first layer (e.g., an inner layer) of the elongate body 408 is provided by a coiled wire of nickel-molybdenum-chromium alloy, such as 35NLT or MP35N. In other embodiments, the wire material can be MP35N LT. In one embodiment, the wire has a 0.008 inch diameter and the coil has a 5 filar right-hand wound construction. The outer diameter of the first layer may be about 0.071 inch. A second layer (e.g., an outer layer) of the elongate body 408 can include the same material as the first layer, disposed on the outside of the first layer. The first and second layers can be wound in the same direction, or in opposite directions. For example, in some embodiments the first layer (e.g., an inner layer) can be left-hand wound and the second layer (e.g., an outer layer) can be right-hand wound, or vice versa. In other embodiments, both the first and second layers can be left-hand wound. In yet other embodiments, both the first and second layers can be right-hand wound. The wound coil wire construction can advantageously facilitate proximal and/or distal flow of infusant along the outer layer of the elongate body 408. For example, the outer layer can be constructed such that the infusant travels along the coil and/or in the direction of the winding. Those skilled in the art may appreciate that, depending on the direction of rotation of the elongate body 408, the infusant flow can advantageously be directed either proximally or distally. The second layer may be a 5 filar left-hand wound construction. In one embodiment, each layer is formed using a 0.008 inch diameter wire, in the above-noted coiled configuration. In other embodiments, the elongate body 408 can include three or more coil wire layers, wherein the layers are wound in alternating directions. In some embodiments, the outer diameter of the second layer can be between about 0.072 inch and about 0.074 inch, while in other embodiments the diameter can be much larger or smaller. In some aspects, for example, the outer diameter of the second layer can be about 0.073 inch. The inner diameter of the elongate body 408 can be at least about 0.039 inch in some implementations. In some embodiments, one or more ends of the elongate body 408 can be welded and square cut, for example, with a 0.1 inch maximum weld length on each end. The length of the elongate body 408 can vary, but in some embodiments, the length can be between about 47 inches and 48 inches, for example, about 47.5 inches.

Other materials and other constructions are possible. The elongate body 408 can be made of other non-ferrous metals or other corrosion resistant material or constructions with appropriate modulus. Other materials that could meet the corrosion requirements include stainless steel (e.g., 302, 304, or 316) and could be used configured with a combination of coil layers, filars, wire diameter, and coil diameter that cause the material to operate below the fatigue stress of the specific material.

In another embodiment, a four layer construction is provided. The four layers comprise three wire-wound layers, e.g., similar to the arrangement described above, but included a third wound layer on the outer surface of the second layer. A low friction layer can be disposed on the outside surface of the elongate body 408. One material that could be used as a low-friction layer is PTFE, known commercially as Teflon®. The low-friction layer should be configured to have sufficient wear resistance, such as by selection of the appropriate PTFE material, e.g. polyphenylene sulphone-filled PTFE, and/or by insuring appropriate infusant flow is maintained during the entire duration of use of the device in order to prevent undesirable local elevated temperature of the PTFE material.

The drive shaft 148 operates within the multilumen catheter body 120. Because the drive shaft 148 is rotated at a very high rate when in use within the multilumen catheter body 120, the configuration of the surface forming the central lumen 286 is important. In various embodiments, this inner surface has high lubricity and high wear resistance. One material that can be used for the inner surface of the catheter body 120 is high density polyethylene (HDPE), which provides sufficient lubricity and wear resistance. In one embodiment, the entire multilumen catheter body 120 is formed of HDPE. PTFE provides good lubricity and could be used if made sufficiently wear resistant. One way to increase the wear resistance of PTFE is to impregnate it with polyphenylene sulphone ($PPSO_2$), another is to gamma irradiate the material. One way to increase the lubricity of Polyimide materials is to impregnate it with Graphite, another is to impregnate it with Graphite and PTFE.

FIG. 4B shows a clearance 412 between the elongate body 408 of the drive shaft 148 and the inner surface of the multilumen catheter body 120. The clearance 412 may be about 0.005 inch. Along a diameter between opposite sides of the inner surface of the central lumen 286 and outer surface of the elongate body 408 includes about 0.010 inch of space or diametric clearance.

FIGS. 11 and 12 show further details of the drive assembly 146, which is disposed at the proximal end 104 of the catheter assembly 100. The drive assembly 146 includes a drive housing 450 having a recess or cavity 454 disposed therein. The cavity 454 is configured for mounting a rotor support shaft 458 for rotation therein. The support shaft 458 has a proximal end and a distal end and a plurality of components mounted thereon. The distal end of the support shaft 458 has a recess 462 formed therein to receive a proximal end of the drive shaft 148. The support shaft 458 may also have a lumen 466 disposed therein for slideably receiving a guidewire.

A rotor 470 is mounted on an outer surface of the support shaft 458 between sleeve bearings 474a, 474b. The rotor 470 can take any suitable form, but in one embodiment includes an elongate magnet 476 disposed between proximal and distal flywheels 478a, 478b.

The proximal end of the support shaft 458 has a tapered port for receiving the guidewire. The proximal end can be configured for engaging the motor 14 in some embodiments. In other embodiments, a magnetic field is induced by the motor 14 in a manner that creates torque and rotation of the shaft 458.

An infusant outflow path 482 is provided within the drive assembly 146. The outflow path 482 is provided between an outer surface of the support shaft 458 and an inner surface 486 of the distal bearing. The flow path 482 continues from the distal bearing 474b radially outwardly along thrust surfaces 490a. The flow path continues proximally between the outer surface of the rotor 470 and the inner surface defining the cavity 454. The flow path 482 continues radially inwardly along the thrust surface 490a toward the support shaft 458. The flow path 482 continues proximally between the support shaft 458 and the proximal bearing 474a. Proximal of the bearing 474a, the flow of infusant exits the catheter assembly 100 through an outflow port 144 through which it can be directed to be is collected in the waste container 46 or discarded. The flow path is shown in more detail in FIGS. 1, 12, 12A, and 12B.

III. Enhancement of Biocompatibility

The heart pump 10 includes various features that enhance the biocompatibility of the pump. For example, the impeller 200 and the housing 202 are carefully configured to interact with the blood in a way that minimizes hemolysis. Also, the blood contacting surfaces and components of the heart pump 10 can be enhanced to minimize adverse effects within the patient.

A. Impeller Configurations

The impeller 200 may be configured to minimize blood hemolysis when in use, while at the same time providing sufficient flow generating performance. FIG. 9 illustrates some configurations in which the work performed by the impeller blades 212, as defined by the flow-pressure performance, is maximized. In FIG. 9, the proximal and distal impeller blades have tips 212a that can have a generally flat configuration. For example, the flat aspect of the distal tips 212a can be disposed at the outermost end thereof. In another embodiment, the tips 212a can have an arcuate shape about the hub 208. More particularly, the arcuate shape can be a helical shape as shown in FIG. 9.

The flat end portion of the tips 212a provides a surface that is generally parallel to the inner wall of the impeller housing 202. In testing, the flat tips 212a have exhibited optimal hydrodynamic performance.

Figure 9A:
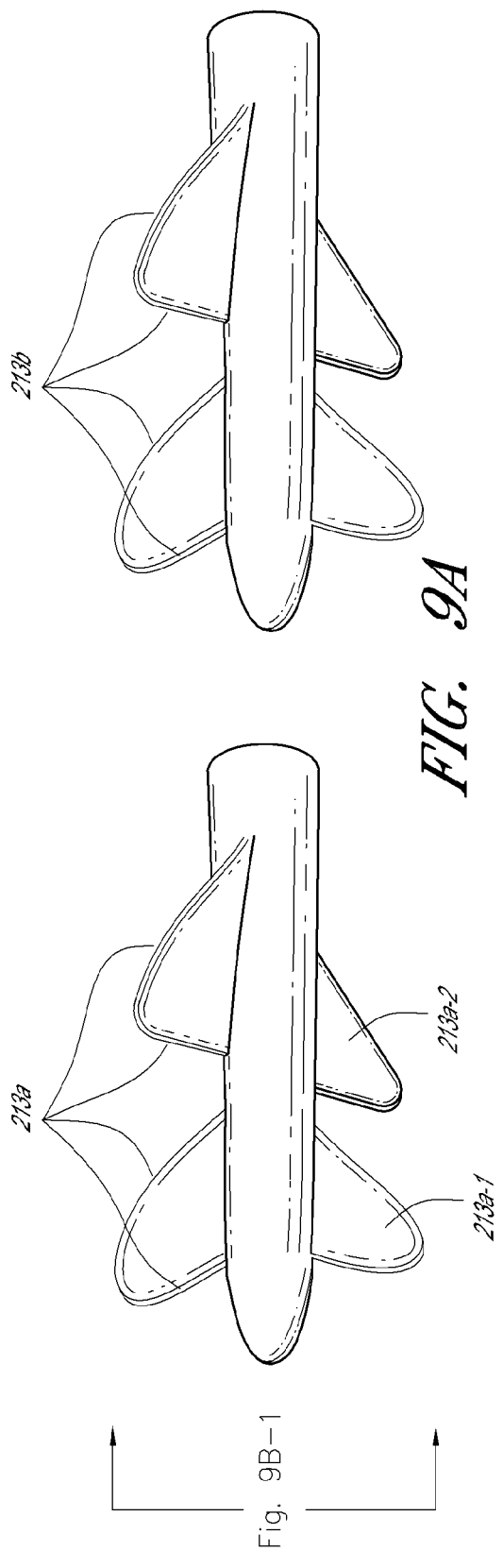

The number of blades 212 on the impeller 200 can vary. For example, the impeller 200 can have one, two, three, four, five, six, or more total blades 212. As illustrated in FIG. 2A, the impeller 200 can have four total blades 212. In another example, the impeller 200 can have two total blades 212. The axial orientation of the blade(s) 212 can vary. In some embodiments, the blades 212 can be arranged axially along the impeller hub 208 in one, two, three, or more rows. As illustrated in FIG. 9A, for example, the impeller 200 can include two blade rows, each row including two blades. A multiple row arrangement may be advantageous in that the maximum amount of time blood components contact the blade is less than is the case with a comparable single row blade configuration. A two row configuration can result in less contact time compared to a single row configuration. In one example, a blade in a single row configuration has an axial length L1. In the two row configuration, the axial distance from the leading edge of the forward blade to the trailing edge of the rearward blade can also be a length L1. A gap between the two blades in the two row configuration can have an axial length of G1. When flowing through the gap, the blood is not in contact with the blades. This short segment or gap of no blood contact with the blades breaks-up the contact time, which provides better handling of delicate structures of the blood. In other embodiments, the impeller 200 can have two blades total, the blades being arranged in a single row (e.g., wherein all of the blades are at generally the same axial position along the impeller hub 208). Advantageously, an impeller 200 with fewer blade rows can be manufactured more easily than an impeller with a larger number of blades and/or a larger number of rows. In addition, an impeller 200 with fewer blade rows can be deployed and/or retrieved more easily than an impeller with additional blade rows. Note that while, in general, FIGS. 9, 9A, 9B-1, and 9B-2 are representative of certain embodiments of blades and impellers, the disclosed blades may have further features not shown to scale. For example, in some embodiments the blades wrap around the shaft such that the leading edge of each blade is off-set by a substantial amount from the trailing edge of the same blade. For example, the leading and trailing edges can be offset by at least about 10 degrees, in some embodiments up to 40 degrees. In other embodiments, the leading and trailing edges are off-set by up to 90 degrees or more. In some embodiments, a first blade had a leading edge at a first circumferential position and a trailing edge at a second circumferential position, and a second blade has a leading edge at a circumferential position between the circumferential position of the leading edge and trailing edge of the first blade.

Figures 1, 9B:
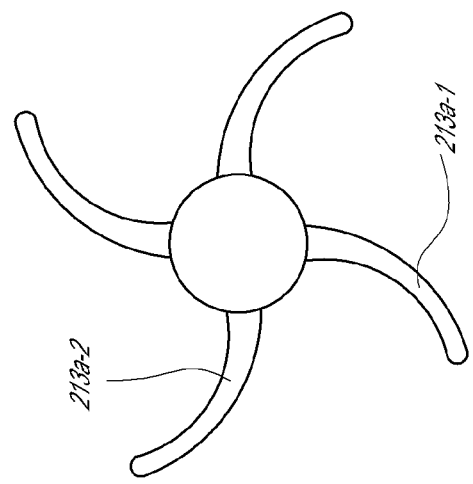
Figures 2, 9B:
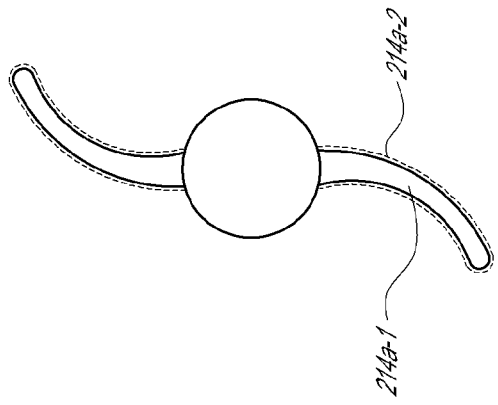

The circumferential orientation of the blade(s) 212 from one row relative to another can also vary. As illustrated in FIG. 9B-1, the blades in the first blade row (e.g., blade 213a-1) can be circumferentially staggered, offset, or clocked, from the blades in the second blade row (e.g., blade 213a-2). In some embodiments, the blades can be fully clocked (e.g., no circumferential overlap between blades). In other embodiments, the blades can be partially clocked (e.g., some circumferential overlap between blades). In yet other embodiments, the blades in the first blade row (e.g., blade 214a-1) can be aligned with the blades in the second blade row (e.g., blade 214a-2), for example as illustrated in FIG. 9B-2. The clocked blades can have many advantages, such as increased flow rate, reduced friction, and/or increased ease of deployment/retrieval.

Figure 10:
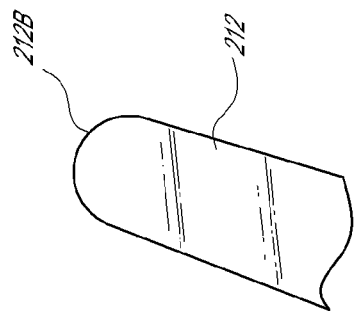

FIG. 10 illustrates another embodiment of an impeller blade 212' that includes modified distal tips 212b. The distal tips 212b are rounded from suction to pressure side of the blade. The rounding of the distal tips 212b can result from eliminating one or more edges between the suction side surface and the pressure side surface. For example as show in FIG. 9, some embodiments provide a plurality of sharp edges between the leading edge, trailing edge, and end surface of the blades. By eliminating one or more of these sharp edges a rounded profile is provided.

Without being bound to any particular theory, it is believed that this rounding reduces fluid stress and fluid stress gradients on the constituents of the fluid being pumped and on the fluid overall. The reduction of such stresses and gradient can provide a more biocompatible interaction of the pump 10 with blood when used as a blood pump. For example, red blood cells can be damaged by being subject to high stresses or to high stress gradients. By reducing exposure of red blood cells to these conditions, hemolysis can be reduced. These benefits can be sustained even where the blades 212' are otherwise arranged to provide equivalent flow performance to the blades 212, such as by providing comparable radial width of the blades 212, 212', rotation speeds, and gaps between the tip 212b and the inner surface of the housing 202.

The configuration of the blades 212' provides the further advantage of reducing sensitivity to the gap between the tip 212b and the inner wall of the housing 202. Where sharp edge configurations are provided, variations in the gap between the tip and the housing wall can greatly affect the flow performance of the pump 10. However, by rounding the edges as in the blades 212', the variation of flow performance is much less due to changing tip gap. Because the housing 202 is flexible and the distal portion of the catheter assembly 100 is disposed in a highly dynamic environment during use this arrangement reduces perturbations in the flow characteristics within the housing 202, providing an even more robust design.

A further advantage of the rounded tip design is that the lessened sensitivity to tip gap provides a better configuration for manufacturing. This arrangement permits wider manufacturing tolerances for one or both of the impeller 200 and the impeller housing 202.

Figure 10A:
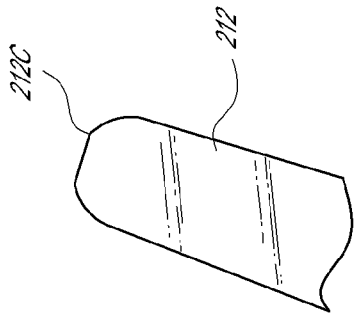

FIG. 10A illustrates further variations of the rounded tip design that combine one or more rounded edges with a flat area 212c at or adjacent the tip of the blade 212". Rounded edges extend from one end of the flat area toward the leading edge of the blade 212" and from another end of the flat area 212c toward the trailing edge of the blade 212". In variations of FIG. 10A, the flat area 212C can be combined with a single rounded edge that extends only toward the leading edge or only toward the trailing edge. One advantage of the combination of the flat area 212c with one or more rounded edges is that this combination maximizes hydrodynamic performance that would occur with a "square edged" tip while providing the benefit of a more gradual change in fluid pressure and fluid stresses resulting in better hemolytic performance that would occur with a rounded tip shape.

FIG. 9A illustrates another embodiment of an impeller blade 213a that includes modified tips 213b. The tips 213b are rounded on the leading edge and trailing edge of the blade. By eliminating sharp edges a rounded profile is provided, in the axial direction. Rounding in this fashion provides the same general benefits as the "cross-blade" tip rounding in 212b, 212c. Without being bound to any particular theory, it is believed that this rounding reduces fluid stress and fluid stress gradients on the constituents of the fluid being pumped. The reduction of such stresses and gradient can provide a more biocompatible interaction of the pump 10 with blood when used as a blood pump. For example, red blood cells can be damaged by being subject to high stresses or to high stress gradients. By reducing exposure of red blood cells to these conditions, hemolysis can be reduced.

B. Coatings to Enhance Biocompatibility

In some embodiments, the impeller 200 can include an outer coating layer (not shown). In some embodiments, the outer coating layer can include one or more polymers. The one or more polymers can include a homopolymer, a copolymer, and/or a mixture of polymers. The one or more polymers can be linear, branched, or crosslinked. The one or more polymers can be thermoset or thermoplastic. In some embodiments, the one or more polymers are elastomeric. In some embodiments, the outer coating layer can be hydrophilic. Examples of suitable polymers include, but are not limited to, silicones (e.g., a siloxane), silanes (e.g., an alkyltriacetoxysilane), polyurethanes, acrylics, and fluoropolymers. One example is a siloxane polymer that has been substituted with one or more alkyl, alkoxy, and/or poly(alkyl amine) groups. Polymers suitable for the outer coating layer can be commercially available and/or synthesized according to methods known to those skilled in the art. Examples of commercially available polymers include the Dow Corning MDX line of silicone polymers (e.g., MDX4-4159, MDX4-4210). In some embodiments, the outer coating layer can also include a therapeutic agent, e.g., a drug that limits the ability of thrombus to adhere to the impeller 200. One example of a suitable therapeutic agent is heparin. In some embodiments, the impeller 200 can include two or more coating layers.

In some embodiments, a substantial portion of the entire exposed surface of the impeller 200 is coated with an outer coating layer. In other embodiments, only a portion of the exposed surface of the impeller 200 is coated with an outer coating layer. For example, in some embodiments, one or more impeller blades 212, or portions thereof, are coated with an outer coating layer.

In some embodiments, the impeller housing 202 can include an outer coating layer (not shown). Suitable materials for the outer coating layer of the impeller housing 202 include, but are not limited to, those described herein with respect to the outer coating layer of the impeller 200. In some embodiments, the impeller housing 202 can include two or more coating layers.

In some embodiments, a substantial portion of the entire exposed surface of the impeller housing 202 is coated with an outer coating layer. In other embodiments, only a portion of the exposed surface of the impeller housing 202 is coated with an outer coating layer. In embodiments where the impeller housing 202 includes a plurality of openings, for example as shown in FIG. 4A, the outer coating layer can coat the impeller housing 202 but not the openings. In other embodiments, the outer coating layer can coat the impeller housing 202 and one or more openings, resulting in a substantially closed impeller housing 202.

The outer coating layer can be applied to the impeller 200 and/or impeller housing 202 by methods known to those skilled in the art, such as dip, spray, or flow coating. The outer coating layer can impart one or more advantageous properties to the impeller 200 and/or impeller housing 202. For example, in some embodiments, an impeller 200 that includes an outer coating layer can exhibit reduced thrombosis, reduced hemolysis, increased lubricity, and/or reduced friction as compared to an otherwise similar impeller that lacks an outer coating layer. Although not bound by theory, it is believed that application of an outer coating layer to the impeller 200 can reduce surface friction, which can improve hemolysis performance by reducing drag forces between the blood and the impeller blades. It is also believed that the outer coating layer can assist in the process of deployment and/or retraction by reducing the coefficient of friction between the collapsed or partially collapsed sliding components.

IV. Debris Capturing Structures

During operation of the heart pump 10, debris can be generated within the system. The debris can comprise particulate matter that is formed by the interaction of separate components of the heart pump, such as in the catheter assembly. For example, when relative motion is provided between two adjacent components in the catheter assembly, such components can contact or rub against each other, causing material to be shaved from the components, thereby generating debris in the form of particulate matter. It can therefore be desirable to remove unwanted debris from the operating components of the catheter assembly. In some aspects discussed herein, the debris is flushed out of the system. In other embodiments, the debris is captured and can remain trapped within portions of the catheter assembly configured to trap debris.

The debris that is generated by the catheter assembly of the heart pump 10 can flow out of the catheter assembly and into a patient, which can be disadvantageous or in some cases detrimental. Furthermore, debris that is generated by the catheter assembly of the heart pump 10 can detrimentally collect at particular areas within the catheter assembly of the heart pump 10, thereby causing increased friction, heat and/or blockage within the catheter assembly of the heart pump 10, such as in channels designed to provide lubrication or other fluid flow. Although adjacent components of the catheter assembly of the heart pump 10 that are in relative motion will be configured to minimize particulate generation, some of the components may operate at very high rates. For example, the impeller assembly 116 and the elongate drive shaft 148 may be rotated at between about 15,000-45,000 revolutions per minute, or between about 25,000-35,000 revolutions per minute. It may be difficult or impossible to configure the catheter assembly of the heart pump 10 to completely eliminate generation of particulate at these and other challenging conditions of use. Accordingly, in some embodiments it is important for the catheter assembly to provide a means to isolate and capture the debris to minimize the risk of debris flowing into a patient or interfering with the operation of the pump 10, such as by blocking a channel within the heart pump.

A heart pump 10 is provided having a catheter assembly with one or more debris capturing structures that are advantageously designed to isolate and capture debris within the heart pump 10. The debris capturing structures can be in the form of spaces or recesses that are formed within the catheter assembly of the heart pump 10 to capture and collect debris generated within the heart pump. In certain embodiments, one or more debris capturing structures in the form of plenums (for example, debris capturing structures 519a and 519b, illustrated in FIG. 13) are formed within the heart pump at select positions along an infusant flow path to minimize passage of debris into static-dynamic interfaces. In some embodiments, the debris capturing structures can also be in the form of one or more walls or baffles positioned in the pump to capture debris generated within the heart pump. The one or more debris capturing structures can be strategically positioned along the length of the pump catheter assembly, such as at points downstream or upstream of key operational components disposed within an infusant fluid path, to capture debris generated within the pump before the debris flows into such components. In some embodiments, the debris capturing structures can be positioned at locations of the pump that may be outside of a patient, such as near the proximal end of the catheter assembly of the pump. The one or more debris capturing structures are advantageously used to capture debris of all sizes, from debris particles to larger debris, to reduce the risk of blockage by the debris in the pump.

Figure 13:
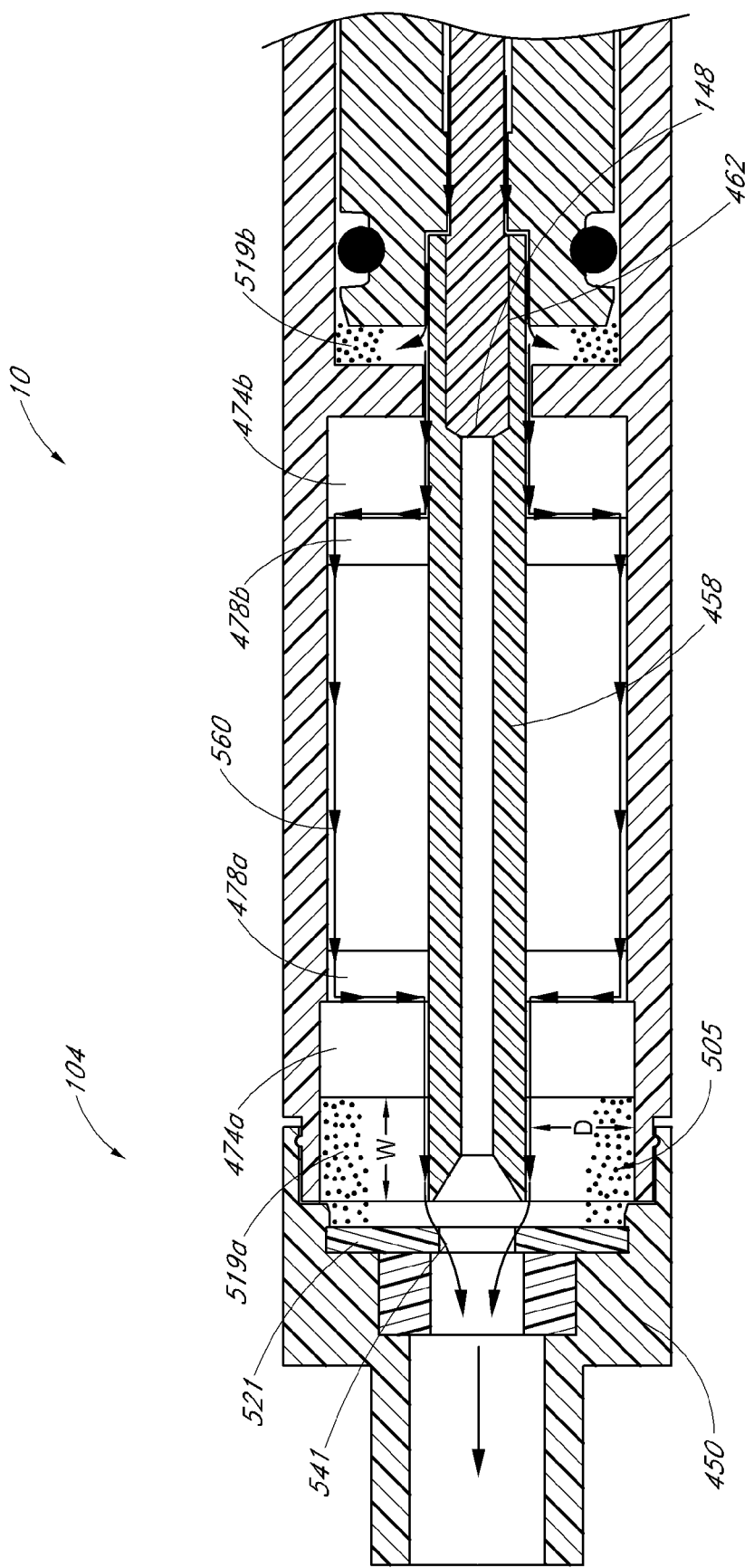
FIG. 13 is a cross-sectional view of a proximal end of the catheter assembly including debris capturing structures.
Figure 14:
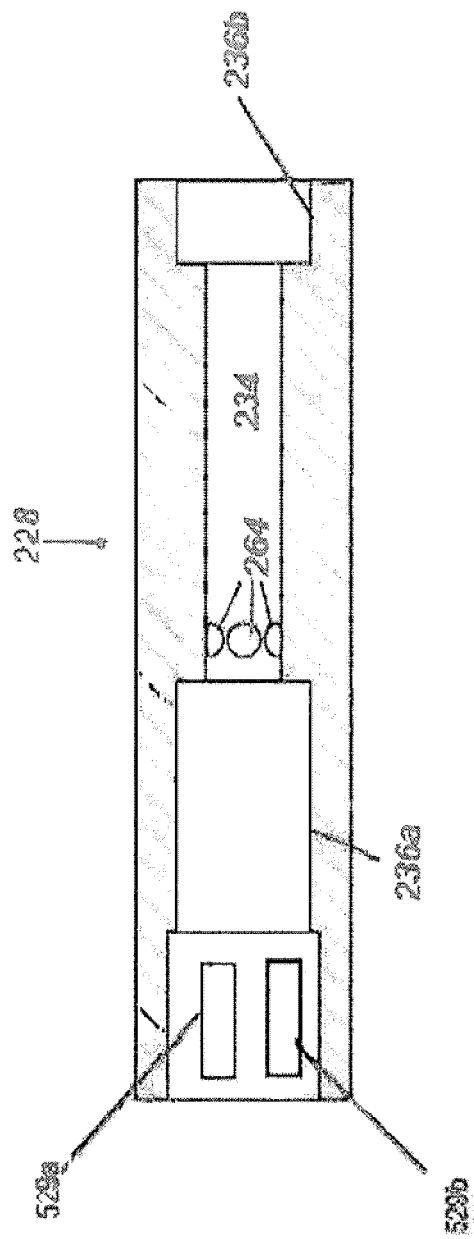
FIG. 14 is a cross-sectional view of a distal portion of the catheter assembly including debris capturing structures.

FIGS. 13 and 14 illustrate cross-sectional side views of a pump catheter assembly including one or more debris capturing structures. FIG. 13 illustrates a cross-sectional view of a proximal end 104 of the catheter assembly of the pump 10 including a drive housing 450 with bearings 474a and 474b, fly wheels 478a and 478b, and debris capturing structures 519a and 519b in the form of recesses. FIG. 14 illustrates a cross-sectional view of a distal portion of the catheter assembly of the pump including bearing housing 228 with enlarged portions 236a and 236b and debris capturing structures 529a and 529b. As illustrated in FIG. 14, the debris capturing structures 529a and 529b can take the form of recesses and can optionally be of different sizes. The debris capturing structures 529a, 529b of FIG. 14 can be positioned near the distal end of the catheter assembly, e.g., near bearings 232a, 232b. As the shaft rotates, debris can be propelled radially outward and can be captured in the debris capturing structures 529a, 529b. In some embodiments, the debris capturing structures 529a, 529b can be spaced longitudinally along the bearing housing 228 and/or circumferentially about the longitudinal axis thereof. While the debris capturing structures 529a, 529b are shown in FIG. 14 as being positioned near the bearings 232a, 232b, in other embodiments, the debris capturing structures 529a, 529b can be positioned longitudinally along the catheter assembly at any other suitable locations for capturing debris.

FIG. 13 illustrates a proximal end 104 of the catheter assembly of the pump including a drive housing 450 having internal bearings 474a and 474b. The proximal end 104 of the catheter assembly of the pump 10 includes a cavity for housing a rotor support shaft 458 for rotation therein. The support shaft 458 has a proximal end and a distal end, with the distal end having a recess 462 formed therein to receive a proximal end of a drive shaft 148. A plurality of channels 560 extend throughout a length of the drive housing 450 to provide one or more fluid flow paths for delivering infusant fluids through the pump body, such as saline. Along the one or more fluid flow paths are a series of debris capturing structures 519a and 519b in the form of recesses that are designed to capture debris generated in the catheter assembly of the heart pump 10. As the support shaft 458 and/or the drive shaft 148 rotate, the centripetal forces can cause debris (e.g., unwanted particles) to flow radially outward and into the debris capturing structures 519a, 519b, thereby separating the debris from the infusant.

The debris capturing structures 519a and 519b comprise plenums, spaces or recesses within the catheter assembly that are configured to capture debris 505 generated in the heart pump. Debris 505 can be generated in the heart pump 10 due to contact between pump components. For example, debris can be generated at the interface between static and dynamic components at a bearing member and within the bearing housing, or as the catheter body is bent to accommodate the tortuous anatomy, friction between the drive shaft or drive cable and inner surface of the conduit (e.g., flush sheath) can cause debris particles to flake from the individual components. Debris 505 that is generated in the heart pump can then flow through the pump catheter assembly via the infusant (e.g., saline). The debris capturing structures 519*a* and 519*b* can be used to capture and isolate the debris 505 generated in the system before the debris flows into a patient or clogs pump components.

The debris 505 can be separated from a liquid medium through centripetal forces generated from rotating components in the pump system such as the support shaft 458 or the drive shaft 148. For example, rotation of the drive shaft 148 can create centripetal forces in the fluid that can spin/move the debris 505 away from the drive shaft 148, where the debris can be isolated from the liquid medium and gathered at these debris capturing structures. Advantageously, according to the present application, the debris 505 can be collected in one or more debris capturing structures 519*a* and 519*b* strategically placed in locations along the catheter assembly. For instance, the debris capturing structures 519*a*, 519*b* can be placed near (e.g., downstream of) various mechanical interfaces, such as bearings and other locations where there is relative motion between parts. As a result, the debris generated by such interfaces can be sequestered before it can come into contact with other moving or small interface components of the system. As described herein, in some embodiments the debris capturing structures 519*a*, 519*b* can be placed near (e.g., upstream of) particular components that benefit from an infusant flow that is substantially debris-free or has a controlled low-level amount of debris, where debris might possibly cause detrimental blockage. For example, in some embodiments, a continuous or persistent flow of infusant can be used to keep blood out of some distal components. A blockage of small passages feeding this infusant distally could result in blood being permitted to enter such distal components.

The debris capturing structures 519*a* and 519*b* can comprise plenums, spaces, or recesses having sidewalls for capturing the debris 505. In some embodiments, the debris capturing structures 519*a* and 519*b* comprise a plurality of recesses having one or more walls that form edges. For example, the debris capturing structures 519*a* and 519*b* can comprise recesses having square edges or rectangular edges. The debris capturing structures 519*a* and 519*b* can assume various shapes. For example, while the debris capturing structures 519*a* and 519*b* can be rectangular with edges, in other embodiments, the debris capturing structures 519*a* and 519*b* can assume shapes other than square or rectangular (e.g., a portion of an upper wall of the debris capturing structures can be rounded). For example, the debris capturing structures can be semi-annular and need not have edges. Advantageously, the sidewalls and edges of the debris capturing structures 519*a* and 519*b* help to capture and trap debris 505 that is generated in the pump.

In addition to assuming various shapes, the debris capturing structures can assume various sizes. For example, as shown in FIG. 13, debris capturing structure 519*a* is larger than the debris capturing structure 519*b*. In some embodiments, the debris capturing structures can be strategically sized based on their position in the pump. For example, in portions of the pump where more debris is expected to be generated, a relatively large debris capturing structure can be provided downstream to collect the debris. In some embodiments, debris capturing structures capable of trapping larger amounts of debris can help to lengthen the duty cycle of a heart pump because the cumulative effect of debris collecting in sensitive areas would be lessened or deferred.

In some embodiments, the debris capturing structures 519*a* and 519*b* can be square or rectangular, as shown in FIG. 13. The debris capturing structures 519*a* and 519*b* can have a width W (e.g., as defined by a dimension extending along the longitudinal/rotational axis of the pump) and a depth D (e.g., as defined by a dimension extending radially away from the longitudinal/rotational axis of the pump). In some embodiments, the debris capturing structures 519*a* and 519*b* can be formed on different sides of the support shaft 458 and/or drive shaft 148, and can be measured by width and diameter. For example, in some embodiments, the debris capturing structures 519*a* and 519*b* can have a width of between about 0.01 inches and 0.3 inches, and a diameter of between about 0.1 inches and 0.7 inches. In the illustrated embodiment in FIG. 13, debris capturing structure 519*a* has a width of about 0.135 inches and a diameter of about 0.4 inches, while debris capturing structure 519*b* has a width of about 0.05 inches and a diameter of about 0.375 inches. One skilled in the art will appreciate that the dimensions are not limited to the ranges above. For example, the diameter of the debris capturing structures could be less than 0.2 inches, so long as it is greater than the length of the normal flow path. One skilled in the art will appreciate, however, that the debris capturing structures need not be limited to the particular shapes and dimensions described herein, as other configurations are also possible. For example, the debris capturing structures can also be comprised of one or more triangular recesses where debris can be trapped in a corner of the triangle. In other embodiments, the debris capturing structures can be semi-annular or shaped like a half-donut. Or, the debris capturing structures can be combination of shapes (e.g., having sidewalls that are representative of a rectangular and a triangular top component).

In an alternate embodiment (shown in FIG. 15A), the debris capturing structures 519*a* and 519*b* can include one or more baffles or walls that extend into a plenum or space to capture debris generated in the pump. The baffles can provide one or more corners or edges where debris can be trapped. In some embodiments, the baffles can form a strategic path that helps to trap debris. For example, a first baffle can be placed against a sidewall of the pump, while a second baffle can be placed adjacent and at an angle to the first baffle, thereby forming a semi-enclosed space for trapping debris.

In some embodiments, to assist in maintaining the debris in the debris capturing structures 519*a* and 519*b*, the debris capturing structures can include one or more veins or pin-sized voids (shown in FIG. 15B) within the sidewalls and/or baffles. Debris that is directed toward the debris capturing structures 519*a* and 519*b* by centripetal force can then be caught or trapped in the smaller veins or voids in the debris capturing structures.

The debris capturing structures can be strategically placed in positions along the length of the pump. In some embodiments, the debris capturing structures are placed at a downstream location of an infusant flow path. The debris capturing structures can be placed downstream of particular components (e.g., downstream from one or more bearings) where debris is likely to be generated, as well as upstream of particular components that benefit from an infusant flow that is substantially debris-free or has a controlled low-level amount of debris, where debris might possibly cause detrimental blockage. For example, in some embodiments, the debris capturing structures can be placed adjacent bearings or flywheels that may make contact with other components of the pump, thereby generating debris. In other embodiments, a flow meter may be provided at the proximal end 104 of the catheter assembly of the pump. Some flow meters operate with components (e.g., structures defining narrow orifices) disposed in the flow stream, which could become blocked by debris. Thus, maintaining a low level of debris or a substantially debris-free flow via the debris capturing structures may extend the life of or enhance the reliability of such flow meters. Acoustic and optical flow meters may be entirely outside the flow stream and may be much less sensitive to failure due to interacting with particulate, and thus benefit less from debris capturing structures.

In some embodiments, one or more sensors can be incorporated in the pump to detect debris blockage in the infusant flow path. The sensors can be used to assess the pressure and/or flow of infusant at certain locations of the infusant flow path to determine whether flow paths are blocked by debris. The sensors can work in conjunction with the debris capturing structures such that debris can be both detected and isolated within the pump.

In some cases, a flow of infusant out of the pump may be maintained free of debris via the debris capturing structures so as to prevent a user from falsely believing that a problem exists within the pump. For example, in embodiments wherein the pump does not include a flow meter, it is still beneficial to provide the debris capturing structures to capture debris from the infusant to prevent dirty infusant outflow into a patient, which could falsely indicate that a problem exists in the pump.

As shown in FIG. 13, in some embodiments, one or more debris capturing structures 519a and 519b in the form of plenums are positioned adjacent to one or more channels 560 that serve as flow paths within the catheter assembly of the pump. The debris capturing structures 519a and 519b can be positioned along the channel flow paths themselves, thereby collecting debris 505 that is carried within infusant moving in the flow paths.

While conventional pumps were unlikely to have debris capturing structures 519a and 519b along the flow paths, especially those with rectangular edges and sidewalls, which are believed to impede continuous flow path, it is observed that even with the debris capturing structures, a continuous flow path can be maintained while providing the added advantage of debris capture. For example, as shown in FIG. 13, debris capturing structure 519a is in the form of a rectangular plenum having a sidewall 521 that is positioned along the infusant (e.g., saline) flow path. In some embodiments, the debris capturing structure 519a can be sized and shaped such that when infusant flows through the channel 560, the infusant can be directed in a radially outward direction upon entering the structure 519a. Debris 505 in the infusant will make contact with the sidewall 521 of the debris capturing structure 519a, and will remain in the debris capturing structure. The infusant can then flow in a radially inward direction toward a fluid outlet 541 adjacent the debris capturing structure sidewall 521. The flow of the infusant through the debris capturing structure 519a is still continuous, but with the added benefit of having debris captured in the debris capturing structure 519a.

As shown in FIG. 13, the debris capturing structures 519a and 519b are placed along the flow path created by the flow channel 560. More specifically, one or more debris capturing structures can be placed adjacent any of the bearings 474a and 474b, fly wheels 478a and 478b, or inner walls of the drive housing 450. While FIG. 13 illustrates a proximal end 104 of the catheter assembly of the pump 10 having two debris capturing structures within the drive housing 450, it is possible to have a single debris capturing structure or more than two debris capturing structures (e.g., three, four, five or more) in this section of the catheter assembly of the pump 10.

As shown in FIG. 13, the debris capturing structures 519a and 519b can be formed on all sides of the catheter assembly of the pump 10, and can be formed on any side of the support shaft 458 and/or drive shaft 148. By having multiple debris capturing structures 519a and 519b and/or debris capturing structures on all sides of the catheter assembly of the pump, this advantageously helps capture and more evenly distribute the collected debris, thereby reducing the risk of debris overfill in the individual debris capturing structures themselves.

FIG. 14 illustrates a distal portion of the catheter assembly of the pump 10 including a bearing housing 228 having enlarged portions 236a and 236b and a lumen 234 extending therethrough. First and second bearings 232a, 232b can be disposed within the enlarged portions 236a and 236b of the bearing housing 228. The distal portion of the catheter assembly of the pump 10 further includes debris capturing structures 529a and 529b in the form of rectangular recesses positioned along a length of the catheter assembly.

Like the debris capturing structures in FIG. 13, the debris capturing structures 529a and 529b of FIG. 14 are positioned along an infusant flow path. While the debris capturing structures 519a, 519b are illustrated in FIG. 13 as being positioned near the proximal end of the catheter assembly, the debris capturing structures 529a, 529b can be positioned near the distal portion of the catheter assembly and can be spaced apart circumferentially. Upon rotation of the drive shaft 148 and/or the impeller shaft 204 in the lumen 234, debris will be forced radially away from the drive shaft 148 by centripetal force and will gather in the debris capturing structures at a particular location (e.g., adjacent bearings) within the pump. The gathered debris are, for example, collected in one of the debris capturing structures 529a and 529b, thereby preventing the debris from obstructing portions of the pump and/or being released into a patient.

While FIG. 14 illustrates that the debris capturing structures 529a and 529b are of similar size, the debris capturing structures need not be of the same size to be effective. Moreover, the debris capturing structures 529a and 529b can be staggered along the length of the catheter assembly. Such a staggering arrangement can advantageously provide an additional opportunity to capture debris along different sections of the catheter assembly of the pump 10 with ease.

FIG. 15A illustrates a cross-sectional side view of a pump catheter assembly including one or more debris capturing structures with baffles. The debris capturing structures 539a and 539b are similar to those shown in FIG. 13, but also include one or more baffles 545 positioned therein. The one or more baffles 545 can assist in partitioning the debris capturing structures 539a and 539b into multiple spaces with additional edges, to further enhance capture of debris. In some embodiments, the baffles 545 can include apertures or veins that serve as openings for receiving debris.

FIG. 15B illustrates a baffle 545 as shown in FIG. 15A with a plurality of pin holes or apertures 570 for assisting in collecting debris. The apertures 570 assist in the capture of debris. When debris particles contact the baffle 545, a portion of the debris can enter into the apertures 570, further helping to trap the debris in the debris capturing structures.

In general, providing multiple cavities within the debris capturing structures 539a, 539b will result in a gradient of particle collection. The location of a cavity (e.g., relative to other cavities in the debris capturing structure) can be configured to increase or decrease the amount of debris that is captured in that particular cavity. For example, the fluid entering the upstream side of the debris capturing structures 539a will have a first greatest concentration of debris and the conditions of the fluid flow in the cavity defined between the upstream side of the plenum 539 and a first baffle 545 may cause some of the particulate to migrate to the periphery in that space. In this arrangement the particulate is captured at the periphery as illustrated in FIG. 15A. As a result, a lesser concentration of particulate will be in the fluid flowing across the baffle 545 into the space defined downstream of the baffle. Due to the lesser concentration of particulate in the fluid flowing into the space defined downstream of the baffle 545, a smaller amount of particulate will collect in the space defined downstream of the baffle. If more than one baffle 545 is provided, each successive space downstream of each successive baffle will collect less and less particulate. As a result, one option is to configure at least one of the successive baffles and spaces disposed immediately downstream of the successive baffles with a lesser particulate collecting capacity. A lesser particulate collecting capacity can be provided by reducing the depth D of successive downstream spaces, reducing the radial dimension or height H of the baffles, or both.

Debris can be permitted to remain in or can be removed from the debris capturing structures 519a and 519b. In some embodiments, the pump walls are provided with ports to the debris capturing structures such that debris can be directly removed from the debris capturing structures (such as via a suction or vacuum). The debris can be removed from the debris capturing structures 519a and 519b either when the pump is turned on or off. In other embodiments, rather than being removed from the pump, the debris can remain in the debris capturing structures for the duration of the pump use. When the pump use is completed and the catheter assembly of the pump is disposed, any trapped debris can be disposed with the catheter assembly of the pump.

In use, infusant can flow distally through the catheter assembly. At least a portion of the infusant (shown by arrows) can return proximally through the catheter assembly, for example as illustrated in FIG. 13. As described further herein, the distal flow rate and the proximal flow rate can be the same or different. In some embodiments, the distal flow rate can be greater than the proximal flow rate. A relatively greater distal flow rate can create an area of positive pressure, thus encouraging at least some infusant to exit the catheter assembly at the distal end thereof (e.g., at or near the impeller). Advantageously, this distally-directed outflow of infusant can minimize or prevent blood from entering one or more components of the catheter assembly. In addition, the distal cavity through which the infusant exits can be sized to reduce or prevent debris from exiting the catheter assembly. Rather, the debris can be contained within the catheter assembly, e.g., within one or more debris capturing structures described herein.

On its return path, once the infusant reaches the distal debris capturing structure 519b, some of the debris flowing with the infusant can be forced radially outward by centripetal forces induced by the rotating drive shaft 148 and/or support shaft 458 into the debris capturing structure 519b, as illustrated in FIG. 13. The infusant can then flow proximally between the bearing 474b and the support shaft 458 in a direction parallel to the longitudinal axis of the catheter. Upon reaching the fly wheel 478b, the infusant can flow radially outward between the fly wheel 478b and the bearing 474b. The infusant can then continue flowing proximally down the channels 560 until reaching the bearing 474a. After reaching the bearing 474a, the infusant can flow radially inward between the bearing 474a and the fly wheel 478a, and can then flow longitudinally between the support shaft 458 and the bearing 474a toward the debris capturing structure 519a.

Those skilled in the art may appreciate that some embodiments may not include a debris capturing structure. As discussed herein, the debris can be removed from the catheter assembly by suction, vacuum, and/or infusant return flow. This configuration may be particularly advantageous for embodiments including one or more disposable components. In these embodiments, debris collection and removal may not be as important, since the disposable component can be replaced before so much debris has accumulated that the operation of the heart pump 10 has been compromised. But for other applications where longer duty cycle is advantageous, debris capturing structures may serve a greater role.

V. Active Pump System for Maintaining Desired Flow or Pressure

The infusant in the infusion system of the heart pump system can serve various functions and provide multiple benefits. Within the pump, infusant can circulate (e.g., via lumens, channels, or spaces 260, 274, 282, 412) thereby helping to cool and lubricate portions of the pump. The circulating infusant can also help insure that any debris generated in the pump is flushed from the pump or moved to a debris capturing structure, the waste container 46, or a filter, as well as assist in pressurizing hydrostatic bearings at relatively high pressures. Furthermore, providing a small amount of infusant flow from the pump and into a patient is one technique for preventing blood from entering areas of the pump that could become damaged due to contact with the blood.

It is thus desirable to maintain a circulating infusant flow into and out of the pump, while also preventing inflow of blood into certain areas of the pump. However, it is difficult to perform these multiple functions using the infusant due to the difficulty in maintaining particular flow and/or pressures of the infusant to perform these functions. For example, while a relatively high flow of infusant can be beneficial for performing functions such as flushing components or pressurizing bearings, controlling relatively high flow to prevent excess infusant from entering the patient may be difficult. It would be desirable to control infusant flow to prevent the back flow of blood into bearings and other areas of the pump. As discussed above, one technique is to cause a controlled amount of infusant flow into the patient to prevent the back flow of blood into the bearings and other areas of the pump.

Figure 16:
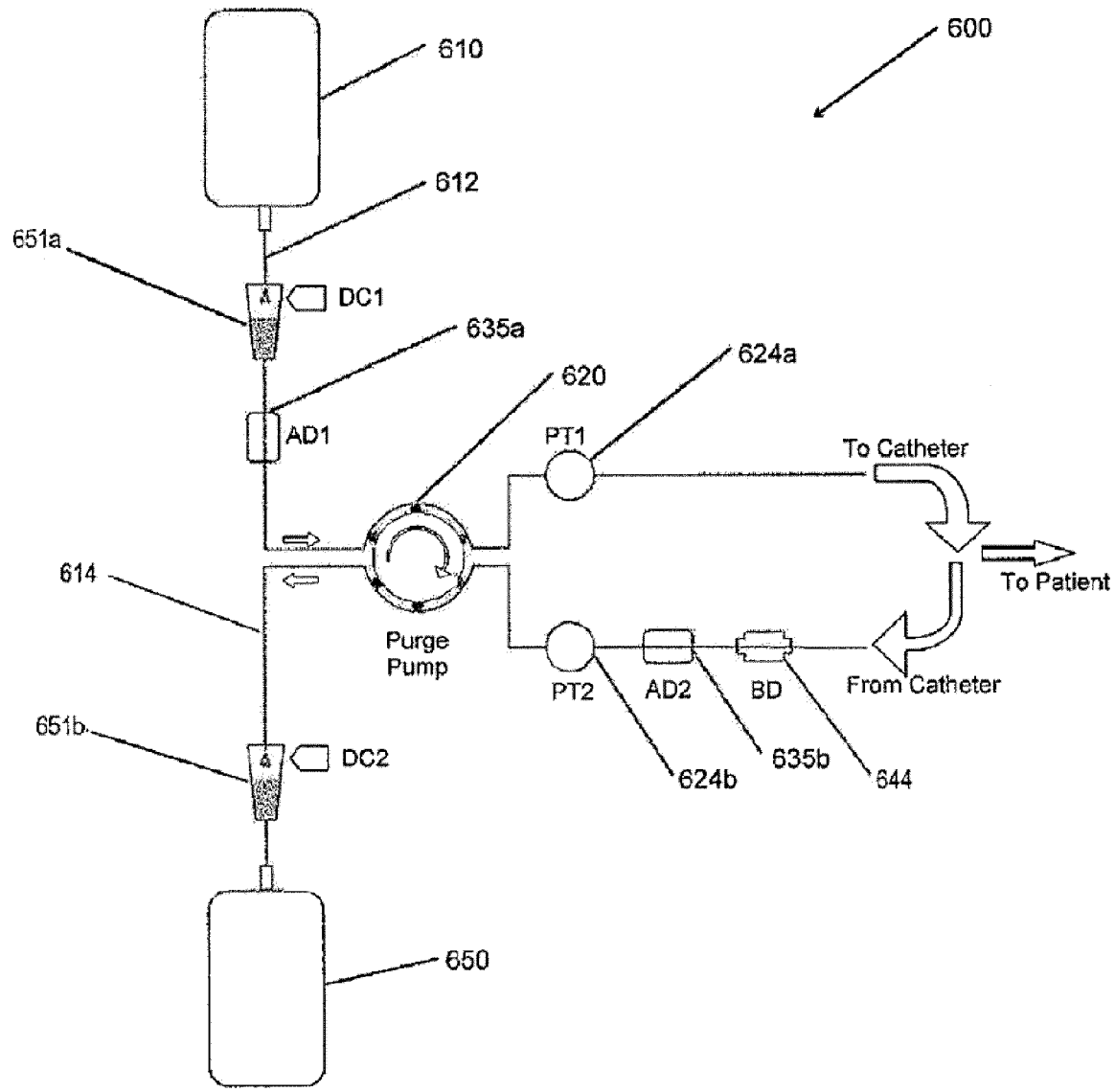
FIG. 16 is a schematic view of one embodiment of a heart pump system with a flow pump assembly for controlling in-flow and out-flow of infusant.

With reference to FIG. 16, in order to maintain a desirable flow of infusant into the patient, while still maintain a circulating infusant flow into and out of the heart pump, an infusion system is provided that controls the flow of infusant into the heart pump through the fluid supply line 612 and the flow of infusant through the fluid return line 614 and out of the heart pump. In some embodiments, the flow in rate through the supply line 612 is greater than the flow out rate through the return line 614, the difference corresponding to flow into a patient, which can minimize or prevent blood from entering sensitive areas of the pump. For example, infusant flows out of the device assembly proximal of the impeller assembly and distal to the catheter body at a region distal to bearing 232B of FIG. 4B, e.g., as shown by arrow 643 in FIG. 4B. The pump system can include one or more flow pumps that regulate the infusion inflow and outflow to provide an amount of infusant into the patient that is large enough to block blood from entering the device but small enough to not be detrimental to a patient.

In some embodiments, the infusion system comprises components for controlling input flow of infusant into the heart pump and/or output flow of infusant out of the heart pump. In some embodiments, a pump can be provided (e.g, along an infusant supply line) to control the flow of infusant into the pump system. Likewise, a pump can be provided (e.g., along an infusant return line) to control the flow of infusant out of the pump system. The flow pumps can include, but are not limited to, syringe pumps, roller pumps, and peristaltic pumps. In some embodiments, a pressure-regulating device (such as a pressure cuff or bag) can also be provided to help adjust the pressure in the system to control infusant input and/or output flow. In other embodiments, the pump system can include a combination of flow pumps or pressure-regulating devices to control the infusant flow into and out of the heart pump, and thus the amount of fluid that enters into a patient.

FIG. 16 illustrates a novel heart pump system for controlling infusant input flow and infusant output flow. The infusion system 600 includes an infusant supply 610, fluid supply line 612, fluid return line 614, pump assembly 620, optional pressure transducers 624a and/or 624b, optional air detectors 635a and/or 635b, optional blood detector 644, waste system 650, and optional flow meters 651a and/or 651b. The fluid supply line 612 runs from the infusant supply 610 to the pump assembly 620, while the fluid return line 614 runs from the pump assembly 620 to the waste system 650.

The pump assembly 620 advantageously regulates the infusant input flow through the fluid supply line 612 and infusant output flow through the fluid return line 614. The pump assembly 620 can comprise a single pump or multiple pumps (e.g., two, three or more) to control the infusant inflow and/or outflow. In some embodiments, the flow pump assembly 620 can include a first pump that maintains a high flow of infusant into the heart pump catheter (e.g., to pressurize the bearings) and a second pump that maintains a high flow of infusant out of the heart pump catheter (e.g., for waste disposal) such that the flow of infusant entering into a patient is desirable. In some embodiments, the flow rate of infusant into the heart pump catheter can be generally the same as the flow rate of infusant out of the heart pump catheter. Those skilled in the art may appreciate that not all of the infusant that flows into the heart pump catheter will flow back out of the heart pump catheter (e.g., because some of the infusant may be released into a patient). Advantageously, in some embodiments, the flow rate of infusant out of the heart pump can be less than the flow rate of infusant into the heart pump, to account for this drop in pressure. In yet other embodiments, the flow rate of infusant out of the heart pump can be greater than the flow rate of infusant into the heart pump. In one embodiment, the flow pump assembly 620 can include a single pump with two or more wheels of differing diameters, wherein each wheel is configured to provide a different flow rate. In another embodiment, the flow pump assembly 620 can include a single pump with two or more tubes of different inner diameters, wherein each tube is configured to provide a different flow rate.

The flow pumps in the pump assembly 620 can help to control either the infusant flow and/or pressure of the system. In some embodiments, the pump assembly 620 can be configured to maintain infusant flow values throughout the system. The pump assembly 620 can be programmed to maintain particular flow rates, such that in some embodiments, the pump assembly 620 will require little if any adjustments during operation. In some embodiments, the flow pumps in the pump assembly 620 can help maintain a steady-state flow of infusant in particular areas of the pump.

In other embodiments, the pump assembly 620 can be configured to maintain particular pressure values within the system. The pump assembly 620 can cooperate with pressure transducers, such as 624a and 624b in FIG. 16, to maintain desired pressure values throughout the system. Should the pressure be higher or lower than desired, the pump assembly 620 can reduce or increase the infusant flow rate to achieve a desired pressure value. For example, a pressure transducer can be provided upstream and adjacent a hydrostatic bearing to ensure that the pressure at the bearing is relatively high; should the pressure be too low, the pump assembly 620 can increase the infusant flow rate and pressure at the bearing.

In some embodiments, the pump assembly 620 can be configured to maintain target pressures, which are required for specific components. For example, it may be advantageous in some instances for hydrostatic bearings to maintain a minimal target pressure in order to meet design goals. The minimal target pressure can vary depending on the clearance within the bearings, and can be achieved with the assistance of the pump assembly 620. In some embodiments, a shunt path around the bearings (not shown) can optionally be provided in order to increase infusant flow rate to downstream components for lubrication and/or cooling of the downstream components, such as the drive shaft. With the pump assembly 620 and shunt path elements, it is possible to regulate a proper amount of infusant pressure and flow to various components in the pump system.

In some embodiments, the pump assembly 620 can be configured to regulate a heart pump's inlet pressure to achieve a target flow. The pump assembly 620 can also be configured to regulate a heart pump's outlet pressure to achieve a target return flow rate. The difference between the inlet flow of infusant into the heart pump and the outlet flow of infusant out of the heart pump is the amount of infusant that enters into a patient. Thus, using the pump assembly 620 advantageously allows control over the amount of infusant that enters into a patient.

In some embodiments, the pump assembly 620 can regulate both infusant flow values and system pressures. For example, the pump assembly 620 can be configured to operate at a constant speed under normal conditions, but can be sped up if inadequate pressure is detected in particular parts of the system (e.g., near bearings).

As shown in FIG. 16, the novel infusion system 600 includes optional pressure transducers 624a and 624b positioned one or more of the fluid supply line 612 and fluid return line 614. The pressure transducers should maintain a sterile system and provide reasonable pressure accuracy. Possible transducers include disposable IBP transducers or other physiological transducers.

The infusion system 600 also optionally includes one or more air detectors, e.g., air detectors 635a and 635b, on either or both of the fluid supply line 612 and fluid return line 614. The air detectors 635a and 635b can advantageously help to detect air entering the system for preventing air embolism in the patient, and also help to ensure that the pumping of infusant is not disrupted. In some embodiments, the air detectors 635a and 635b can be clipped onto in the infusant inflow and outflow tubing. In some embodiments, the air detectors can include ultrasonic air detectors.

The infusion system 600 optionally includes a blood detector 644 positioned along the fluid return line 614. The blood detector 644 can be used to determine whether blood has entered into components (e.g., bearing) of the blood pump, which could cause malfunctioning of the heart pump. If blood is detected by the blood detector 644, the clinician may advantageously be notified to take the pump 10 out of service or replace the catheter assembly 100. In some embodiments, blood detection can be performed by colormetric means. In some embodiments, the blood detector 644 can be a BLD-06 blood detector, manufactured by Introtek.

The infusion system 600 further includes optional flow meters 651a and 651b designed to measure the infusant flow in the fluid supply line and/or the infusant flow in the fluid return line. The flow meters 651a and 651b can be in the form of drop counter sensors which can measure flow by counting drops per unit time in drip chambers. The flow meters 651a and 651*b* can help the flow pump assembly 620 to adjust flow and pressure depending on the values read in the flow meters.

Figure 16A:
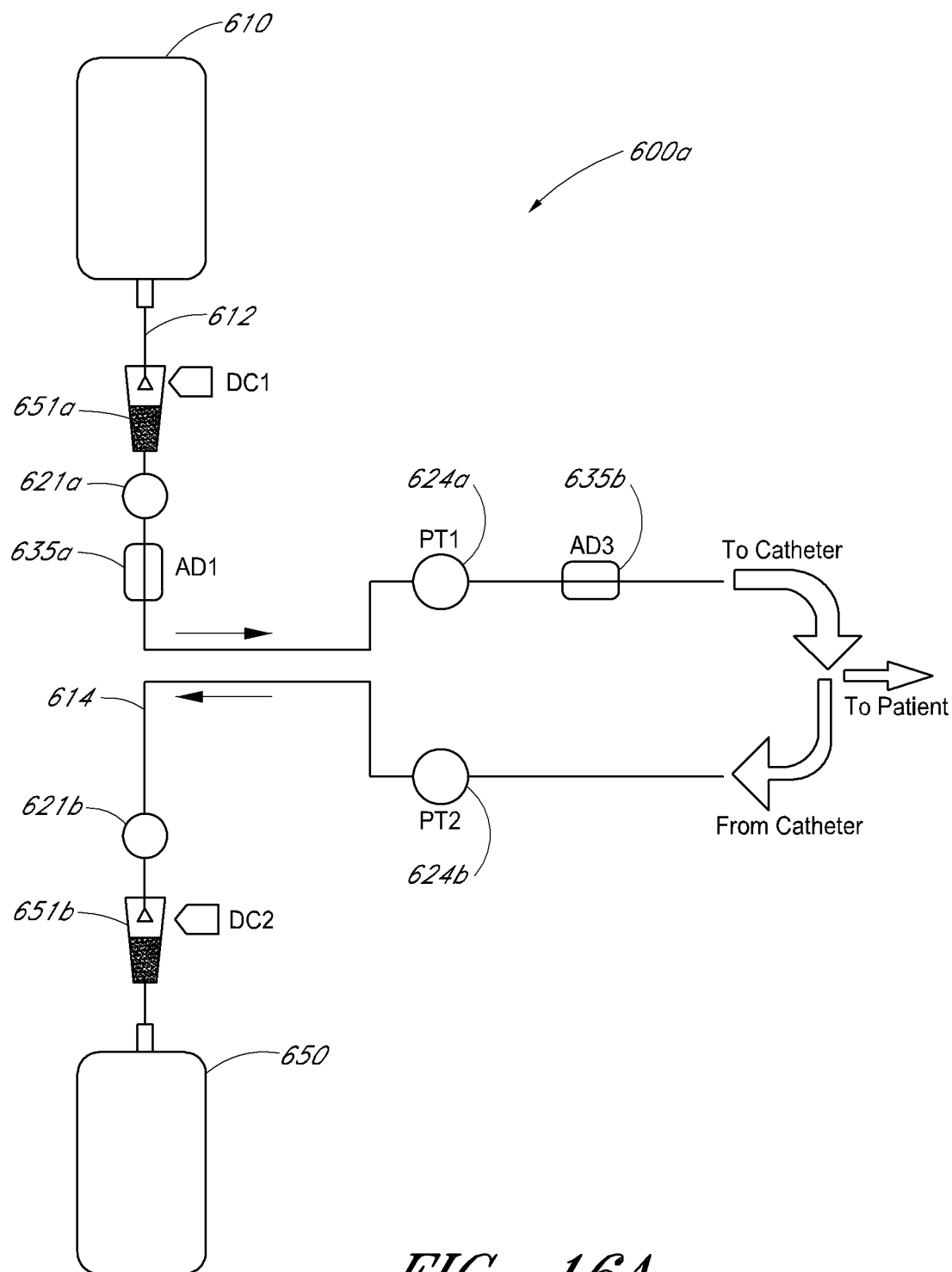
FIG. 16A is a schematic view of other embodiments of a heart pump system with a flow pump assembly for controlling in-flow and out-flow of infusant.

FIG. 16A illustrates another embodiment of the infusion system 600*a*. In this embodiment, the pump assembly 620 can include an inflow pump 621*a* and an outflow pump 621*b*. The inflow pump 621*a* can be connected to the fluid supply line 612 and the outflow pump 621*b* can be connected to the fluid return line 614. Advantageously, the inflow pump 621*a* and the outflow pump 621*b* can be configured to operate separately and/or independently from one another. For example, the inflow pump 621*a* and the outflow pump 621*b* can be configured to operate at different flow rates.

As illustrated in FIG. 16A, the air detector 635*a*, in communication with the fluid supply line 612, can be positioned within the same fluid channel as, e.g., downstream of, the inflow pump 621*a*. Advantageously, the optional air detector 635*a* can detect any air or bubbles that may have been introduced upstream thereof, such as where bubbles are introduced into the infusant by an upstream component, such as the inflow pump 621*a*. The infusion system 600*a* illustrated in FIG. 16A additionally includes an air detector 635*c* that is also in communication with the fluid supply line 612 and that is positioned between the pressure transducer 642*a* and the catheter. Advantageously, this second air detector 635*c* in communication with the fluid supply line 612 provides redundancy to further reduce the risk of air embolism.

The infusion system 600*a* illustrated in FIG. 16A may not include the blood detector 644 or the air detector 635*b* on the fluid return line 614. Otherwise, the infusion system illustrated in FIG. 16A can include many, if not all, of the components and advantages of the infusion system 600 illustrated in FIG. 16.

Advantageously, each of the components in FIGS. 16 and 16A help to control system pressure and/or fluid flow to provide a desirable infusant flow in and out of the pump system, as well as into the patient.

In addition, the novel heart pump system can include components (e.g., detectors and sensors) that serve as diagnostic tools to assess the performance of the heart pump. In some embodiments, sensors can be placed along both a fluid supply line and/or a fluid return line to detect variations in pressure and/or flow of infusant. The changes that are detected can be used to assess the performance of the heart pump (e.g., infusion system) and determine whether problems exist in the heart pump (e.g., whether there is blockage by debris or leakage). For example, if a sudden pressure drop is detected (e.g., at the fluid return line) in the heart pump, this can be an indication that a leak exists in the pump system. Or, if a sudden pressure increase is detected (e.g., at the fluid supply line) in the heart pump, this can be an indication that the infusant flow path is clogged by debris. Assessments can likewise be made with increased and decreased flow rates. In some embodiments, the assessments can be made in realtime, or with minimal delay. Advantageously, the diagnostic tools can cooperate with the pump assembly 620 discussed above to regulate the infusant flow and pressures based on the diagnostic assessments. For example, a decrease in flow rate at the supply or return line may indicate a blockage or a leakage in the system. In some embodiments, the detected pressure and flow measurements may be used in combination to determine the performance of the pump system. Detection via sensors of unexpected changes in pressure or flow of infusant into the patient can generally help to diagnose problems in the pump system.

VI. Valve Arrangement to Prime Heart Pump

Before or during the flow of infusant into the heart pump, it is beneficial to "prime" the heart pump by removing or expelling air from the device. Removing air from the heart pump can help to reduce the amount of air bubbles in the system, which can be detrimental to maintaining proper blood and/or infusant flow. The priming of the heart pump can occur before the heart pump is placed in a patient.

To remove air from the heart pump, infusant can be introduced into the heart pump to physically displace air. The infusant is used to physically direct and force air out of an aperture (e.g., located at the distal tip at the base of the impeller hub). For example, in conventional heart pumps, infusant can flow down an infusant delivery flow path to physically direct air to exit an aperture. The infusant can either exit the aperture or can continue to flow down an infusant return flow path. In conventional pumps, the infusant return flow path is not being utilized as a path to infuse fluid to direct air towards the distal aperture, and air can detrimentally remain within the heart pump, including along the infusant return flow path. On the contrary, in the present system, a purge pump is used to drive infusant from a reservoir into a circuit, flow/flushing through components and moving parts of the blood pump, pushing/expelling air, debris into a waste container while lubricating the moving parts (e.g., drive shaft) and preventing blood from entering the circuit simultaneously. The removal of the air from the heart pump can occur prior to introducing the pump into a patient.

To enhance the expulsion of air from the heart pump, a novel pump system can be provided that utilizes both the infusant delivery flow path and the infusant return flow path to expel air from the system. The pump system includes a novel valve arrangement that is provided between the infusant delivery flow path and the infusant return flow path to temporarily route the infusant input flow path to the return flow path. By routing the infusant delivery flow path to the return flow path, this creates a short between the delivery flow path and return flow path. Infusant can then flow down both the delivery flow path and the "return" flow path such that the infusant can force and displace the air (e.g., in the flow paths) to exit an aperture or clearance in the heart pump 10, such as at or in the impeller hub 208 (see FIG. 3). The aperture or clearance can be located at the distal tip at the base of the impeller hub 208. By providing an infusant flow path down both the delivery flow path and return flow path, air can be displaced and expelled out of the one or more apertures. The air is thus removed via both the delivery flow path and what would ordinarily be the "return" flow path to rapidly and effectively expel air from the system.

The process of expelling air will be performed prior to insertion of the catheter assembly 100 of the heart pump 10 into the patient if the air is expelled through a portion that would be disposed within the patient in use to avoid air embolism. The heart pump can be held vertically (e.g., with the distal tip of the impeller 208 upward) so that air bubbles can float out the appropriate apertures prior to inserting the heart pump into the patient. Such vertical priming can prove especially advantageous to remove air to prime the device, as the air can be both pushed out by infusant and can float out of the heart pump. In other embodiments, air expulsion can also take place during operation of the heart pump.

Figure 17A:
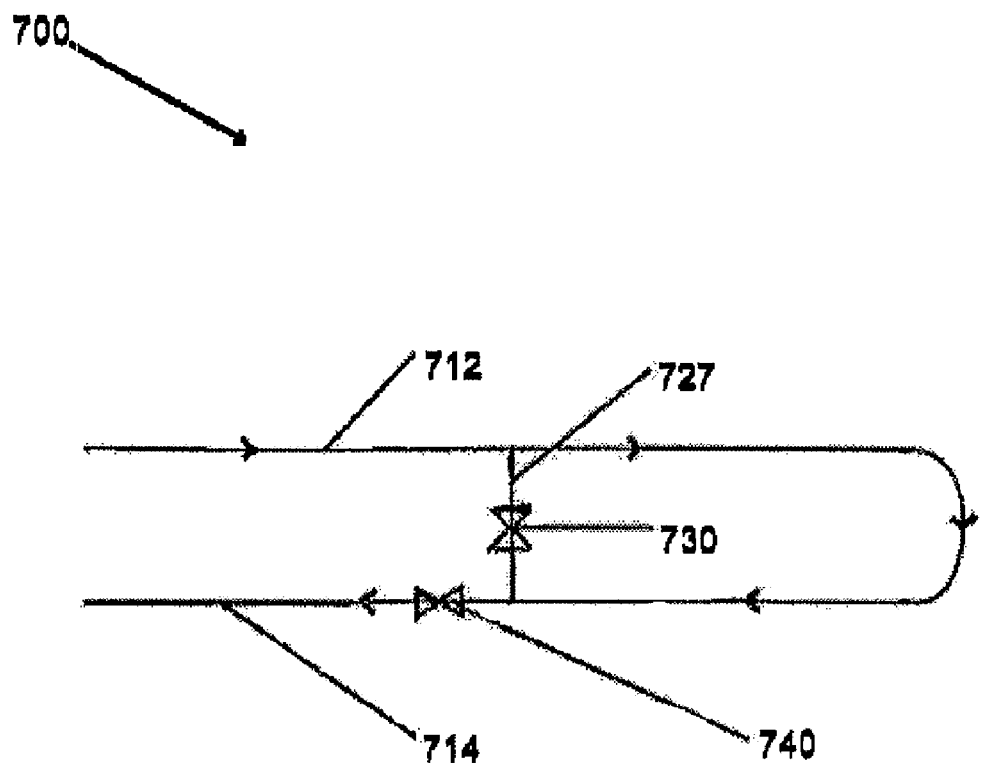
FIG. 17A is a schematic view of a valve arrangement with non-operable shunt.
Figure 17B:
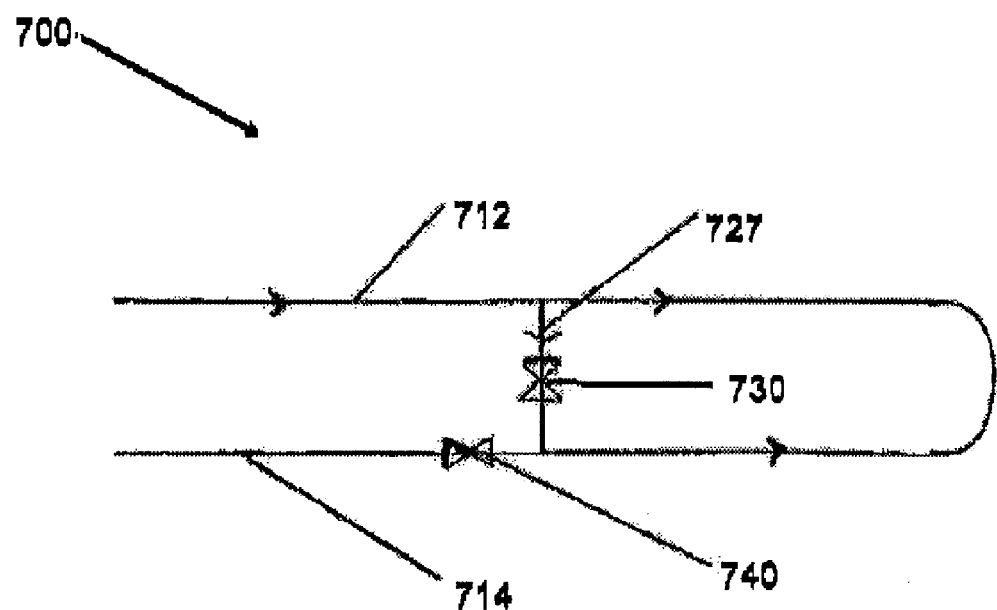
FIG. 17B is a schematic view of a valve arrangement with operable shunt.

FIGS. 17A and 17B illustrate another embodiment of an infusion system 700 for a heart pump that has a novel valve arrangement in which an infusant delivery flow path 712 and an infusant return flow path 714 are connected via a shunt 727 by having an optional shunt valve 730. An optional additional outflow valve 740 can be positioned along the infusant return flow path 714. FIG. 17A illustrates a conventional flow route with the optional shunt valve 730 closed and inoperable. FIG. 17B illustrates a novel flow route with both the shunt valve 730 open and operable and the additional outflow valve 740 closed, in which air can be directed down both the infusant delivery flow path 712 and the infusant return flow path 714 for expulsion out of a catheter body (not shown). The infusion system 700 advantageously allows air to be expelled from the heart pump prior to introducing the pump into a patient.

FIG. 17A illustrates a conventional flow route with the optional shunt valve 730 closed and the shunt 727 inoperable, such that a short is not created between the infusant delivery flow path 712 and the infusant return flow path 714. As shown by the arrows in FIG. 17A, infusant can flow into the infusant delivery flow path 712, through a pump catheter body, and out of the infusant return flow path 714. While in this configuration, some air may be removed from the pump catheter body, air that is not removed from the pump catheter body can be trapped (such as along the infusant return flow path 714) rather than expelled.

FIG. 17B illustrates an improved flow route with the optional shunt valve 730 open and the shunt 727 operable, such that a short is created between the infusant delivery flow path 712 and the infusant return flow path 714. In addition, optional valve 740 can also be closed, thereby blocking the conventional pathway of the infusant return flow path 714. As shown by the arrows in FIG. 17B, this valve arrangement allows infusant to flow down the infusant delivery flow path 712, as well as down the shunt 727 and down the infusant return flow path 714. The infusant can flow down both the delivery flow path 712 and the return flow path 714 to physically displace air towards an aperture at a distal end of the heart pump, whereby the air can be expelled from an aperture (e.g., at the distal tip of an impeller). The shunt 727 thus provides multiple pathways via which the infusant can flow to displace the air and expel it from the catheter.

In some embodiments, the infusant flow down the infusant delivery flow path 712 and the infusant return flow path 714 can differ due to the differences in the flow paths and any restrictions (e.g., walls or baffles) therein. Accordingly, in some embodiments, the shunt 727 includes a component to modulate the flow (e.g., down the infusant return flow path 714) to accommodate any differences in the infusant flow that may affect air expulsion. For example, the shunt 727 can include a mechanical wall that can be raised or lowered to different heights to increase or decrease the amount of infusant flow that is delivered through the shunt pathway.

In alternative embodiments, to expel air from the pump, infusant can be introduced into both an inflow port (e.g., connected to the delivery flow path 712) and an outflow port (e.g., connected to the return flow path 714). In some embodiments, the flow of infusant into the inflow port and the outflow port can be simultaneous, sequential, or both. By introducing infusant into both an inflow port and an outflow port, the infusant can displace air along two separate pathways, thereby helping to make the priming process more efficient. The use of the shunt to create a short between the delivery flow path 712 and the return flow path 714 is optional in this embodiment.

In alternative embodiments, the above valve arrangement with shunt 727, shunt valve 730 and outflow valve 740 can also be accompanied by a first pump provided to regulate in-flow of the infusant and a second pump provided to regulate out-flow of the infusant. Advantageously, when the shunt 727 is operable and the outflow valve 740 is closed, the second pump can also be turned off, thereby helping to redirect infusant and air down the infusant return flow path 714. Even if the outflow valve 740 is not yet closed, the second pump can still be turned off in order to help redirect infusant and air down the infusant return flow path 714.

The novel valve arrangement with shunt can be provided anywhere between the infusant delivery flow path and the infusant return flow path. For example, with respect to FIG. 16, the valve arrangement with shunt can be provided downstream of the pump assembly 620 to connect the fluid supply line 612 to the fluid return line 614. The novel valve arrangement advantageously helps to provide a faster and more effective means to "prime" and expel air from the pump device prior to or during use.

Other alternative embodiments may not include a shunt 727. In at least some of these embodiments, trapped air can exit the heart pump both at a distal end (e.g., adjacent the impeller assembly) and at a proximal end (e.g., by way of the proximal flow of infusant traveling along the return flow path 714).

In some embodiments, the flow rates of infusant during the priming process can be different than the flow rates of infusant during operation. In some embodiments, the flow rates of infusant can be higher during the priming process due to the desire to displace and expel columns of air from out of the heart pump. Once air has been removed from the heart pump, the flow rates of the infusant can be reduced. In some embodiments, during the priming process, it may be desirable to operate the impeller at a very low speed to assist in expulsion of air bubbles from the system.

VII. Methods

As discussed above, in various embodiments the heart pump 10 is inserted in a less invasive manner, e.g., using techniques that can be employed in a catheter lab. Various general techniques pertinent to the heart pump 10, which can be combined with the methods and techniques discussed above, are described in U.S. patent application Ser. No. 12/829,359, filed on Jul. 1, 2010, and entitled Blood Pump With Expandable Cannula, which is incorporated by reference herein in its entirety and for all purposes.

It will be apparent to those skilled in the art that various modifications and variations can be made in the present embodiments without departing from the scope or spirit of the advantages of the present application. Thus, it is intended that the present application cover the modifications and variations of these embodiments and their equivalents.

What is claimed is:

1. A heart pump system comprising:
   an elongate catheter body;
   an impeller disposed at a distal portion of the elongate catheter body;
   one or more bearings positioned between the catheter body and the impeller;
   a fluid supply line for delivering infusant into the catheter body;
   a fluid return line for transporting infusant out of the catheter body and out of a patient; and
   an infusion system comprising a pump for regulating the infusant flow along the fluid supply line and fluid return line.

2. The heart pump system of claim 1, wherein the infusion system pump is configured to regulate the pressure of an inlet of the heart pump to achieve a target flow rate.

3. The heart pump system of claim 2, wherein the infusion system pump is configured to regulate the pressure of an outlet of the heart pump to achieve a target return flow rate, wherein the difference between the target flow rate and target return flow rate is deposited into the patient.

4. The heart pump system of claim 1, further comprising one or more pressure transducers for cooperating with the infusion system pump.

5. The heart pump system of claim 1, further comprising one or more air detectors.

6. The heart pump system of claim 1, wherein the infusion system pump assembly comprises two or more pumps.

7. The heart pump system of claim 6, wherein a first pump is in communication with the fluid supply line and a second pump is in fluid communication with the fluid return line.

8. A heart pump system comprising:
an elongate catheter body;
an impeller disposed at a distal portion of the elongate catheter body;
one or more bearings positioned between the catheter body and the impeller;
an infusant delivery flow path for delivering infusant into the catheter body;
an infusant return flow path for transporting infusant out of the catheter body and out of a patient; and
a pump priming structure.

9. The heart pump system of claim 8, further comprising a shunt and a valve for regulating flow through the shunt, wherein the shunt is connected between the infusant delivery flow path and the infusant return flow path.

10. The heart pump system of claim 9, wherein the shunt is configured such that when it is open, air can be diverted from the infusant delivery flow path into the infusant return flow path.

11. A heart pump comprising:
a catheter assembly comprising a proximal end, a distal end, and an elongate body extending therebetween;
an impeller disposed distal to the catheter assembly;
an infusant flow channel disposed within the catheter assembly for directing infusant through the catheter assembly; and
at least one recess positioned along the infusant flow channel, wherein the recess is configured to capture debris generated in the catheter assembly.

12. The heart pump of claim 11, wherein the recess is positioned adjacent a bearing.

13. The heart pump of claim 11, wherein the recess comprises a recess or plenum.

14. The heart pump of claim 11, wherein the edge of the recess comprises a portion of a square or rectangular structure.

15. The heart pump of claim 11, wherein the recess comprises a baffle that partitions the recess.

16. The heart pump of claim 11, comprising a first recess and a second recess, wherein the first recess and the second recess are of different sizes.

17. The heart pump of claim 16, wherein the first recess is located in a different position along the length of the catheter assembly from the second recess.

18. The heart pump of claim 16, where the first recess is located distal of an infusant introduction port and the second recess is located proximal of the infusant introduction port.

19. The heart pump of claim 11, wherein the infusant flow channel has an upstream and a downstream direction in use and wherein the recess is located in the upstream direction from and immediately adjacent to a load bearing interface.

20. A heart pump comprising:
an elongate catheter body;
an impeller disposed at a distal portion of the elongate catheter body;
one or more bearings positioned between the catheter body and the impeller, at least one of the bearings comprising a surface facing a portion of the impeller;
an inflow channel disposed within the elongate catheter body for directing infusant to the surface of the bearing (s) facing the impeller, wherein a first portion of infusant is directed in a proximal direction from a distal inflow port disposed adjacent to the bearing(s) and a second portion of infusant is directed in a distal direction from the distal inflow port;
an outflow channel for directing infusant away from the surface of the bearing(s); and
at least one recess configured to capture debris and positioned along the outflow channel downstream of the one or more bearings.

21. The heart pump of claim 20, wherein the recess is configured to separate debris from infusant upstream of a hydrodynamic bearing.

22. The heart pump of claim 20, wherein the recess is configured to separate debris from infusant upstream of a fluid boundary induced by an interface between a moving component and a static component of the heart pump.

23. The heart pump of claim 22, wherein the moving component comprises an elongate drive shaft and the static component comprises an inner wall of the elongate catheter body, the inner wall surrounding an inner lumen in which the drive cable rotates.

* * * * *